United States Patent
Gilad-Gilor et al.

(10) Patent No.: US 11,298,013 B2
(45) Date of Patent: Apr. 12, 2022

(54) APPARATUS AND METHODS FOR PERFORMING BODY IMAGING

(71) Applicant: TYTO CARE LTD., Netanya (IL)

(72) Inventors: David Gilad-Gilor, Even Yehuda (IL); Uri Dubin, Haifa (IL); Eyal Bychkov, Hod Hasharon (IL)

(73) Assignee: TYTO CARE LTD., Netanya (IL)

( * ) Notice: Subject to any disclaimer, the term of this patent is extended or adjusted under 35 U.S.C. 154(b) by 0 days.

(21) Appl. No.: 15/540,645

(22) PCT Filed: Dec. 28, 2015

(86) PCT No.: PCT/IL2015/051258
§ 371 (c)(1),
(2) Date: Jun. 29, 2017

(87) PCT Pub. No.: WO2016/108229
PCT Pub. Date: Jul. 7, 2016

(65) Prior Publication Data
US 2018/0000336 A1    Jan. 4, 2018

Related U.S. Application Data

(60) Provisional application No. 62/098,549, filed on Dec. 31, 2014.

(51) Int. Cl.
| | | |
|---|---|---|
| *A61B 1/227* | (2006.01) | |
| *A61B 1/00* | (2006.01) | |
| *A61B 1/005* | (2006.01) | |
| *A61B 5/00* | (2006.01) | |
| *A61B 5/021* | (2006.01) | |

(Continued)

(52) U.S. Cl.
CPC .............. *A61B 1/227* (2013.01); *A61B 1/005* (2013.01); *A61B 1/0011* (2013.01); *A61B 1/00071* (2013.01); *A61B 1/00142* (2013.01); *A61B 5/6817* (2013.01); *A61B 1/00016* (2013.01);

(Continued)

(58) Field of Classification Search
CPC ............ A61B 1/00087; A61B 1/00096; A61B 1/00165; A61B 1/06; A61B 1/227; A61B 1/233; A61B 1/24
See application file for complete search history.

(56) References Cited

U.S. PATENT DOCUMENTS

| | | | | |
|---|---|---|---|---|
| 3,840,004 A | * | 10/1974 | Heine ................... | A61B 1/227 600/200 |
| 4,335,713 A | * | 6/1982 | Komiya ................. | A61B 1/227 600/114 |

(Continued)

FOREIGN PATENT DOCUMENTS

| | | |
|---|---|---|
| CN | 101541238 A | 9/2009 |
| CN | 102038481 A | 5/2011 |

(Continued)

*Primary Examiner* — Eduardo C Robert
*Assistant Examiner* — Steven J Cotroneo

(57) ABSTRACT

An otoscope, comprising: (a) a flexible speculum, operable to be inserted into an ear canal; (b) a stopper, coupled to the flexible speculum, operable to limit penetration depth of the flexible speculum into the ear canal; and (c) an imaging sensor, located inside the flexible speculum, operable to capture an image of an eardrum of the ear canal; wherein a flexibility of the flexible speculum allows alignment of the imaging sensor according to a shape of the ear canal.

20 Claims, 14 Drawing Sheets

(51) Int. Cl.
*A61B 5/01* (2006.01)
*A61B 5/332* (2021.01)

(52) U.S. Cl.
CPC ............... *A61B 5/01* (2013.01); *A61B 5/021* (2013.01); *A61B 5/332* (2021.01)

(56) References Cited

U.S. PATENT DOCUMENTS

| | | | | |
|---|---|---|---|---|
| 4,380,998 | A * | 4/1983 | Kieffer, III | A61B 1/2275 128/864 |
| 5,469,855 | A * | 11/1995 | Pompei | G01J 5/04 374/121 |
| 8,066,634 | B2 * | 11/2011 | Andreassen | A61B 1/227 600/112 |
| 8,781,574 | B2 * | 7/2014 | Pless | A61B 1/00135 607/2 |
| 9,736,342 | B2 * | 8/2017 | Mueckl | H04N 5/2252 |
| 10,004,386 | B2 * | 6/2018 | Ruppersberg | A61B 1/00142 |
| 2001/0014112 | A1 * | 8/2001 | Yamaka | G01J 5/02 374/158 |
| 2002/0038076 | A1 * | 3/2002 | Sheehan | A61B 1/00055 600/200 |
| 2002/0085616 | A1 * | 7/2002 | Yu | G01J 5/02 374/158 |
| 2002/0193665 | A1 * | 12/2002 | Jones | A61B 1/00105 600/200 |
| 2005/0143626 | A1 * | 6/2005 | Prescott | A61B 1/00087 600/162 |
| 2011/0015489 | A1 * | 1/2011 | Raghuprasad | A61B 1/227 600/187 |
| 2012/0059224 | A1 * | 3/2012 | Wellen | A61B 1/2275 600/200 |
| 2015/0351607 | A1 * | 12/2015 | Ruppersberg | A61B 5/01 600/473 |
| 2018/0125345 | A1 * | 5/2018 | Rebella | A61B 1/227 |

FOREIGN PATENT DOCUMENTS

| | | |
|---|---|---|
| CN | 102159276 A | 8/2011 |
| CN | 102711584 A | 10/2012 |
| CN | 202723816 U | 2/2013 |
| WO | 2004105607 A2 | 12/2004 |
| WO | 2009029504 A2 | 3/2009 |
| WO | WO 2014/117955 A2 | 8/2014 |

* cited by examiner

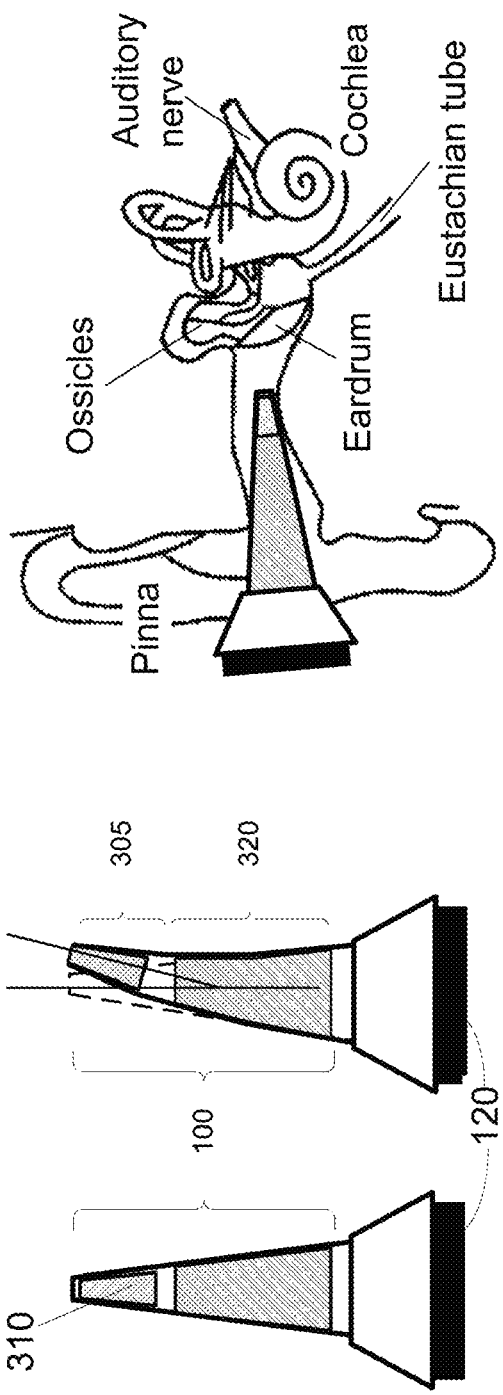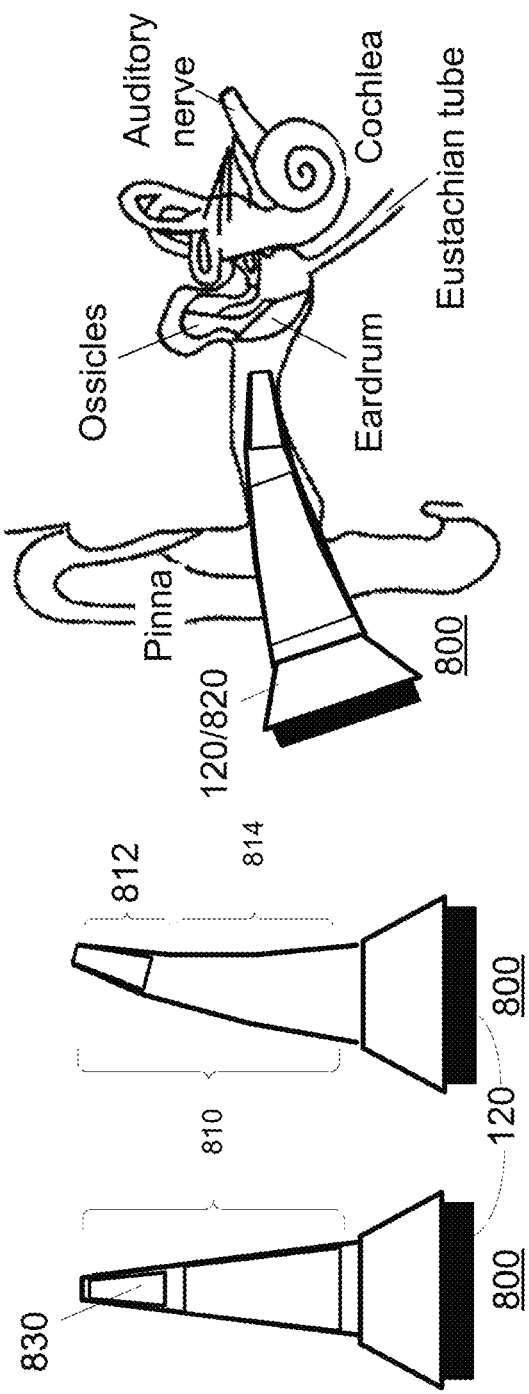
FIG. 8A
FIG. 8B

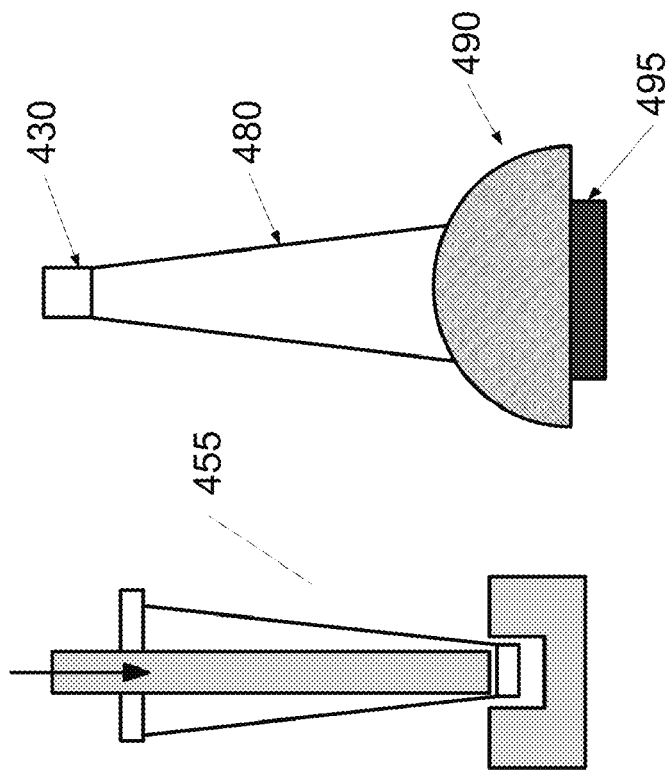
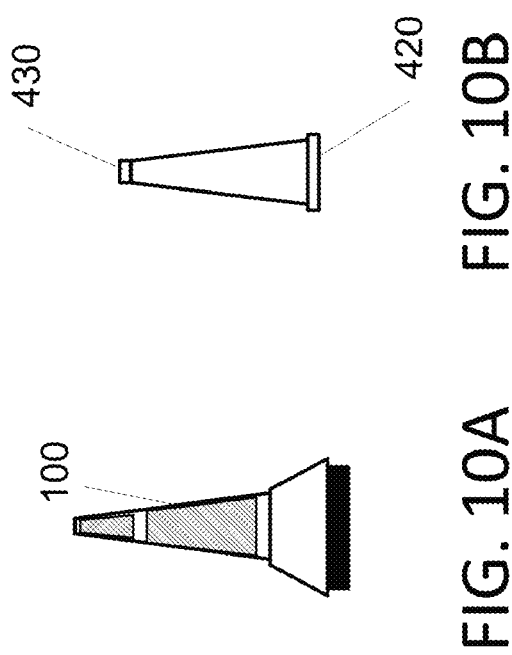
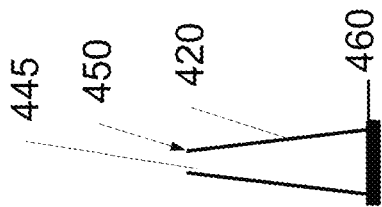
FIG. 10A  FIG. 10B
FIG. 10C
FIG. 10D
FIG. 10E

```
                                    1530
  Inserting a flexible speculum into an ear canal, so that the inserting
  causes bending of the flexible speculum inside the ear canal, thereby
  aligning an imaging sensor included in the flexible speculum according
                         to a shape of the ear canal
```

```
                                    1590
  After the imaging sensor captures an image of an eardrum of the ear
          canal, removing the flexible speculum from the ear canal
```

FIG. 16A       1500

```
                                    1530
   Inserting a flexible speculum into an ear canal, so that the
   inserting causes bending of the flexible speculum inside the
   ear canal, thereby aligning an imaging sensor included in
   the flexible speculum according to a shape of the ear canal
```

```
   1610 Capturing one or more
   images of the eardrum by the
              imaging sensor
```

```
                                    1590
   After the imaging sensor captures an image of an eardrum
   of the ear canal, removing the flexible speculum from the
                             ear canal
```

```
   1610 Capturing one or more
   images of the eardrum by the
              imaging sensor
```

FIG. 16B       1500

1510
Determining the allowed penetration depth of the stopper into the ear canal

1512 Mechanically configuring a penetration depth limit allowed by the stopper (which is connected to the flexible speculum and which limits a penetration depth of the flexible speculum into the ear canal)

1514 Selecting a stopper out of a plurality of different stoppers, and connecting the selected stopper to the flexible speculum, for limiting a penetration depth of the flexible speculum into the ear

1520 Covering the flexible speculum, prior to the inserting, with a flexible cover which includes an optical tip which allows transmission of light through the optical tip to the imaging sensor

1530
Inserting a flexible speculum into an ear canal, so that the inserting causes bending of the flexible speculum inside the ear canal, thereby aligning an imaging sensor included in the flexible speculum according to a shape of the ear canal

1540
Stopping the insertion of the flexible speculum into the ear canal when a stopper connected to the flexible speculum limits further penetration of the flexible speculum into the ear canal

1590
After the imaging sensor captures an image of an eardrum of the ear canal, removing the flexible speculum from the ear canal

APPARATUS AND METHODS FOR PERFORMING BODY IMAGING

RELATED APPLICATIONS

This application claims priority from U.S. provisional patent application Ser. No. 62/098,549 filing date 31 Dec. 2014 which is incorporated herein by reference in its entirety.

FIELD OF THE INVENTION

The invention relates generally to the field of body imaging and examination and more particularly to devices and methods for enhancing and improving the quality and usability of imaging process.

BACKGROUND OF THE INVENTION

Ear exams are one of the most commonly performed medical examinations. In the United States alone there are about 30 million ear examinations every year. Currently most of these examinations are usually performed by health professionals using standard medical tools such as analogue or digital otoscopes. The otoscope is often used by a trained physician to look at particular components of a patient's ear, including the outer ear canal and eardrum. Most otoscopes are handheld devices. These devices usually include a simple light source, one or more magnifying lens, and a speculum, an often hard plastic funnel-shaped viewing piece. Speculums can be covered by disposable hard-plastic liners for hygienic and/or other reasons.

In recent years trends within telemedicine and consumer based healthcare have evolved substantially, allowing cost reduction, improved efficiency of the basic healthcare services and the ability to provide quality services remotely. Stand-alone devices and tools used by clinicians today are often too expensive, specialized and/or difficult to operate to appeal to consumers. Often the functionality and design of those tools can limit the capability of performing an effective and easy examination by an untrained consumer.

Handheld mobile devices, such as cellular phones, tablets, phablets, wearable technologies, smartwatches, PDA's, and other devices are becoming increasingly useful for imaging due to their ready availability to communicate with other devices wirelessly. However, the cameras and illumination sources included with most mobile electronic devices are primitive with respect to the type of imaging that may be required for special surfaces such as a patient's skin or body passage like the ear canal.

Cellscope Inc. of San Francisco develops a speculum which connects to a smartphone, together operating as an otoscope. The website of the company can be found at https://www.cellscope.com/.

Welch Allyn, Inc. of New York develops a digital otoscope with USB communication. Additional information can be found the website of the company, e.g. at http://www.welchallyn.com/en/products/categories/physical-exam/ear-exam/otoscopes-macroview/macroview-otoscope.html.

Another digital otoscope with a flexible USB connection is developed my MISUMI Corporation. Additional information can be found the website of the company, e.g. at http://www.misumi.com.tw/PLIST.ASP?PC_ID=57.

SUMMARY

According to an aspect of the invention, there is disclosed an otoscope, including
a) a flexible speculum, operable to be inserted into an ear canal;
b) a stopper, coupled to the flexible speculum, operable to limit penetration depth of the flexible speculum into the ear canal; and
c) an imaging sensor, located inside the flexible speculum, operable to capture an image of an eardrum of the ear canal;
d) wherein a flexibility of the flexible speculum allows alignment of the imaging sensor according to a shape of the ear canal.

According to an aspect of the invention, there is disclosed a method for intraaural imaging, the method including:
a) inserting a flexible speculum into an ear canal, so that the inserting causes bending of the flexible speculum inside the ear canal, thereby aligning an imaging sensor comprised in the flexible speculum according to a shape of the ear canal; and
b) after the imaging sensor captures an image of an eardrum of the ear canal, removing the flexible speculum from the ear canal;

BRIEF DESCRIPTION OF THE DRAWINGS

In the drawings and descriptions set forth, identical reference numerals indicate those components that are common in different drawings.

Elements in the drawings are not necessarily drawn to scale. It should be noted that the figures are given as examples only and in no way limit the scope of the invention. Like components are denoted by like reference numerals.

Figure 1A:
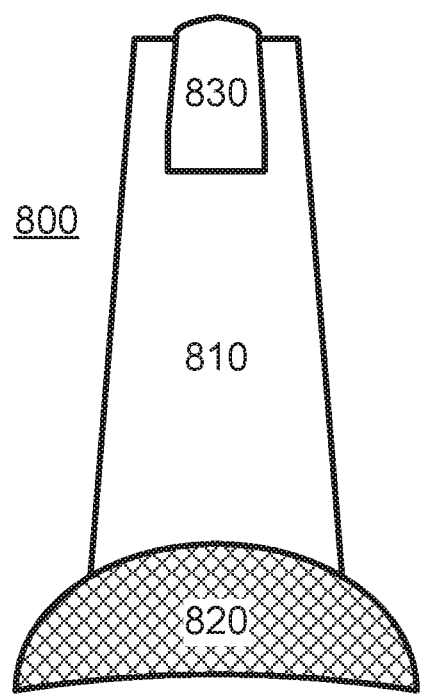

For example, the dimensions of some of the elements can be exaggerated relative to other elements for clarity. Further, where considered appropriate, reference numerals can be repeated among the figures to indicate corresponding or analogous elements.

Figure 2:
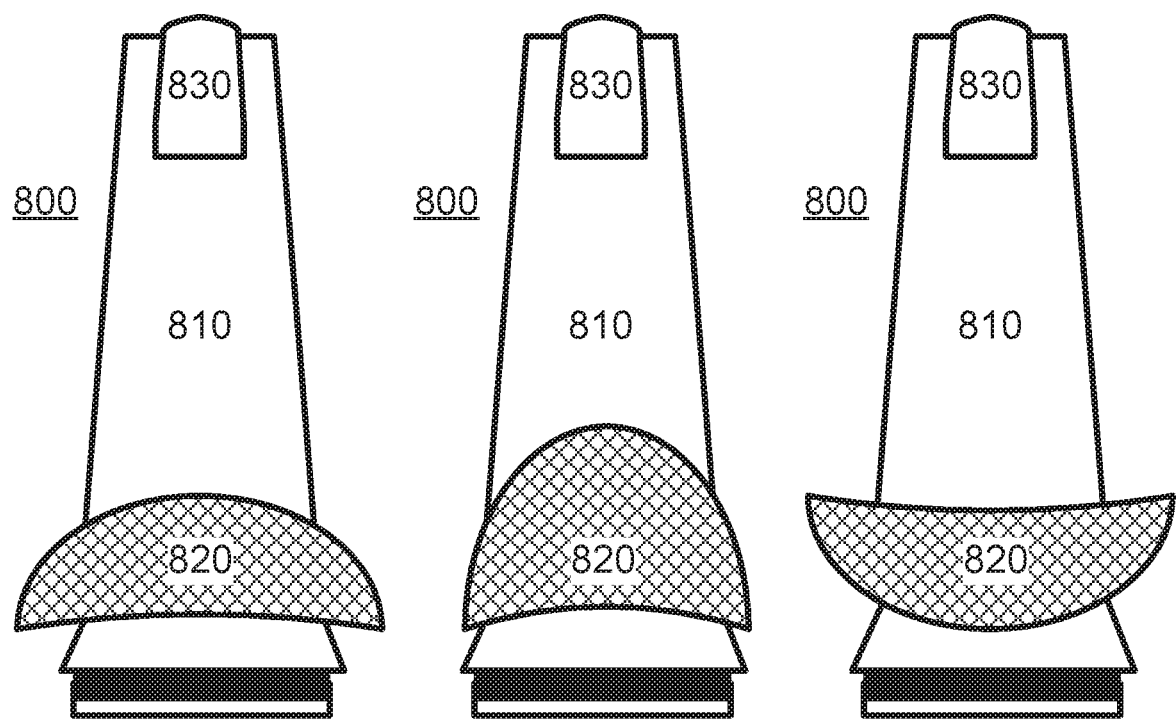
Figure 3:
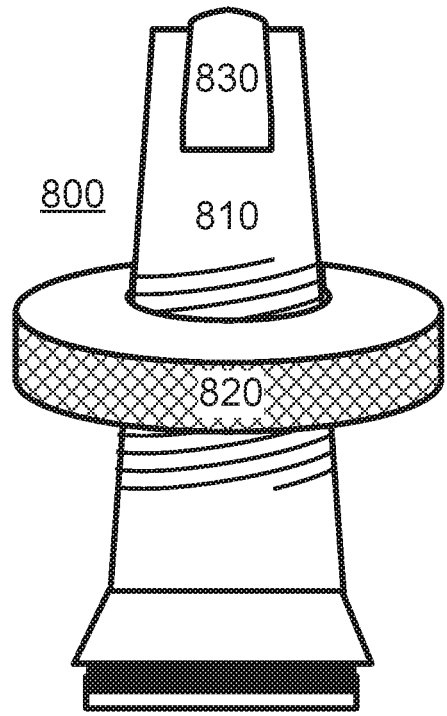
Figure 5:
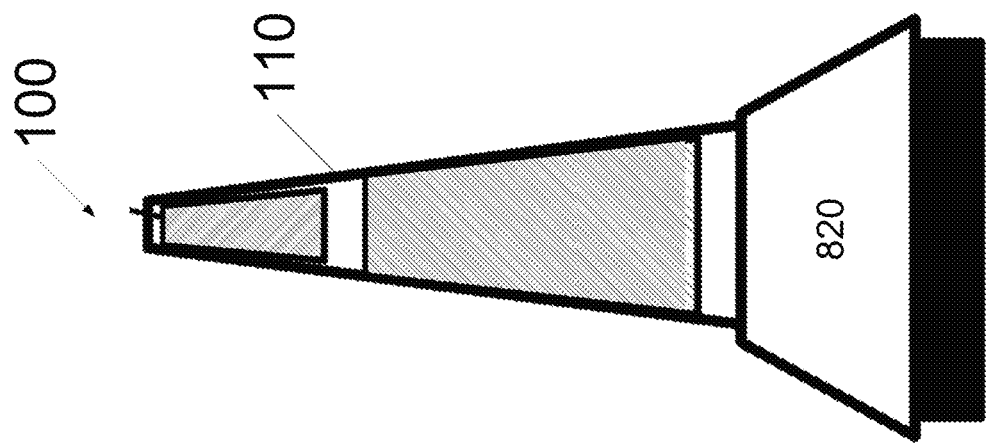
Figure 4B:
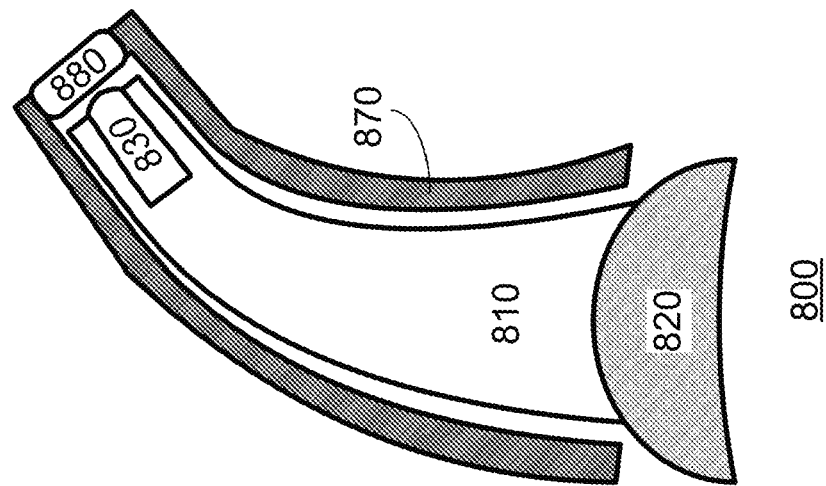
Figure 4A:
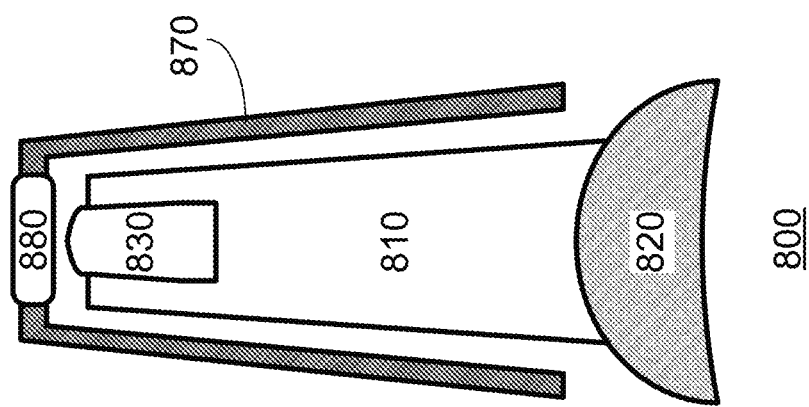
Figure 6A:
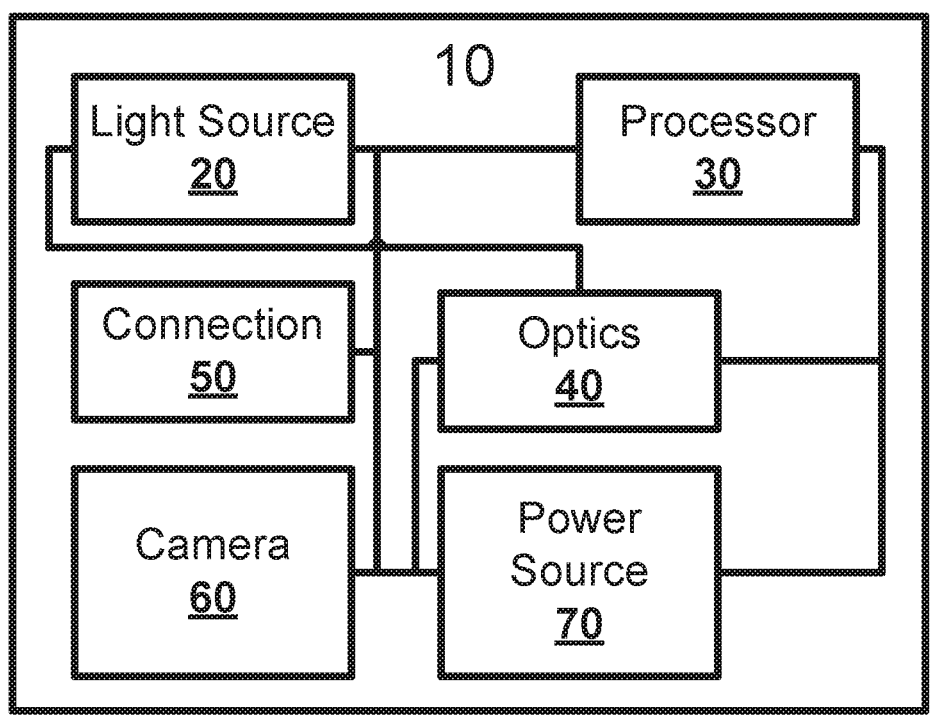
Figure 6B:
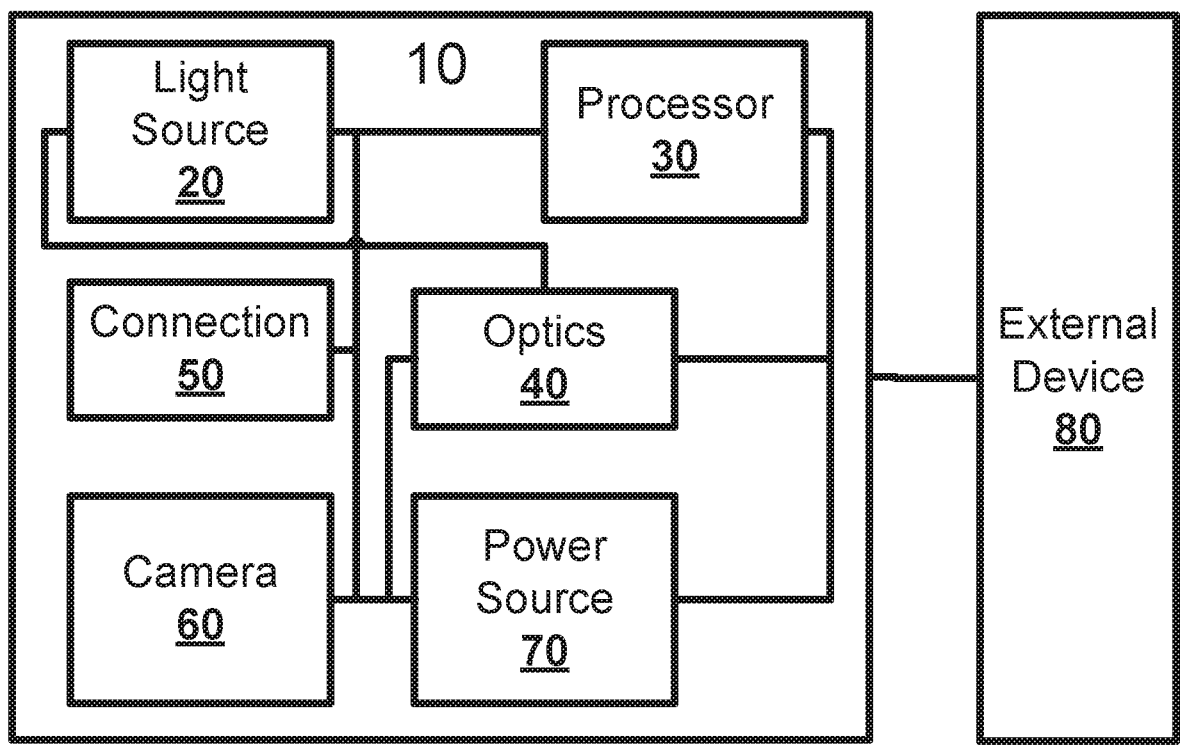
Figure 7A:
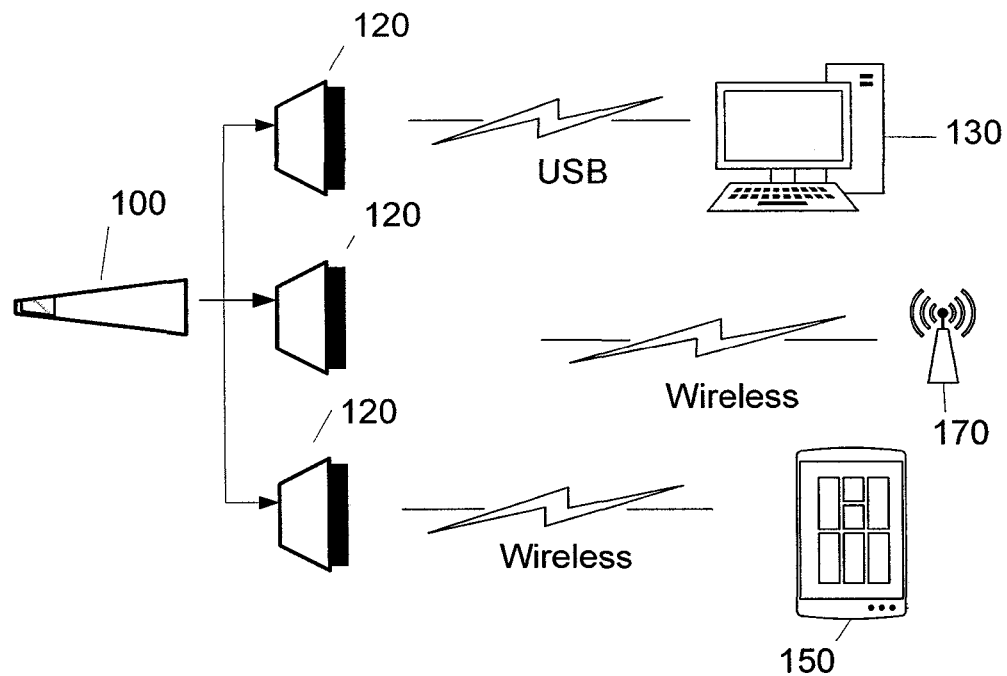
Figure 7B:
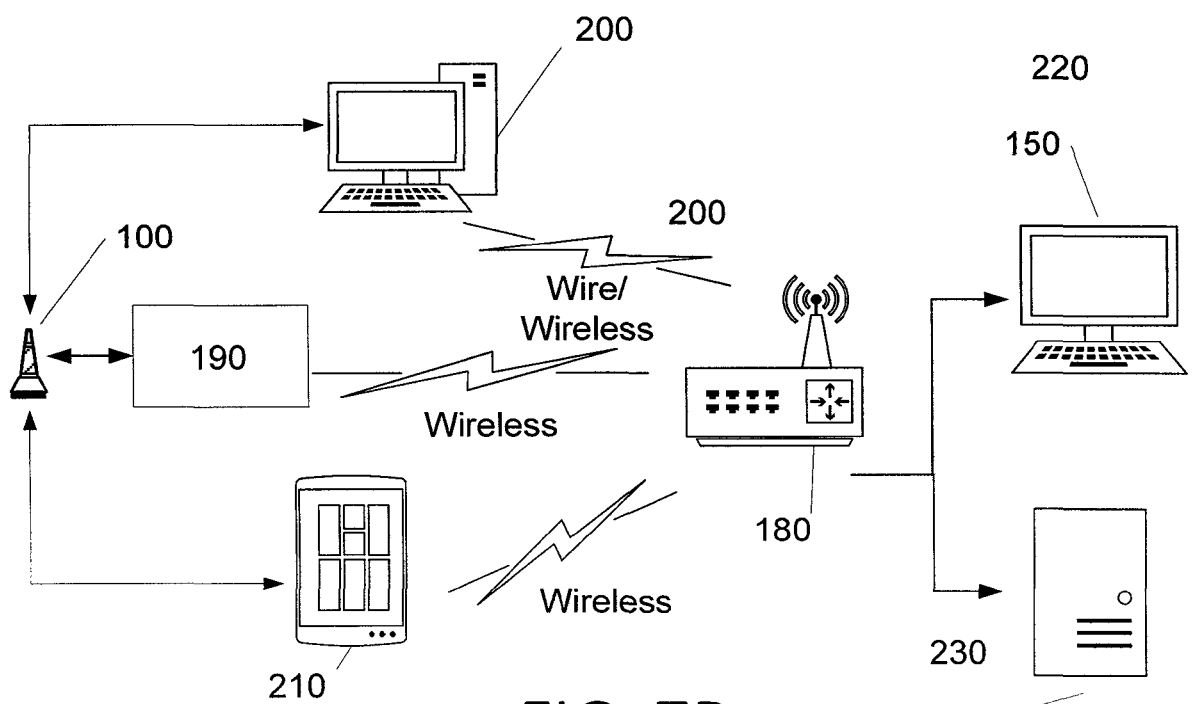
Figure 9A:
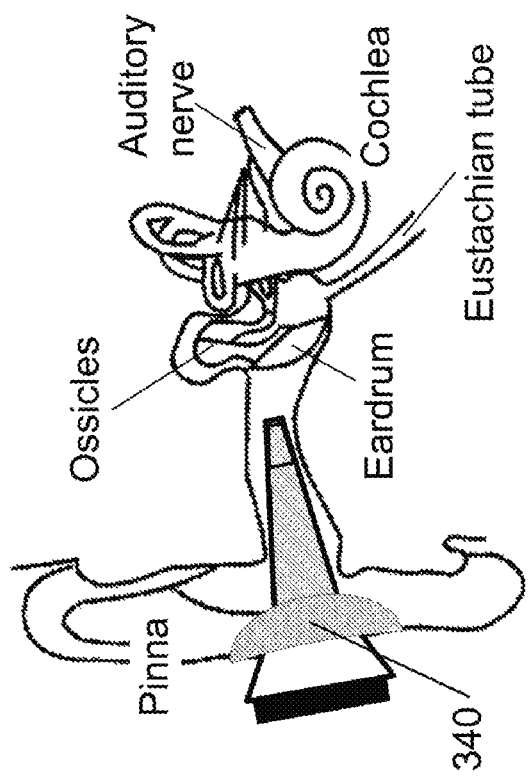
Figure 9A:
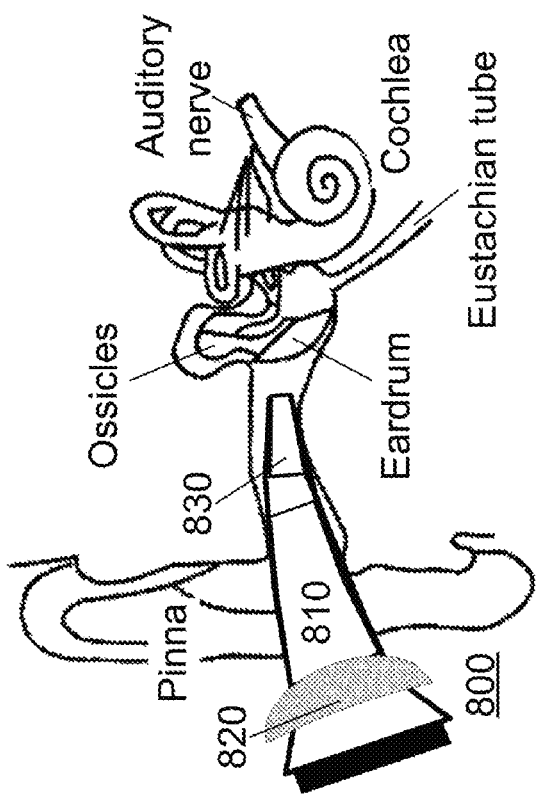
Figure 9A:
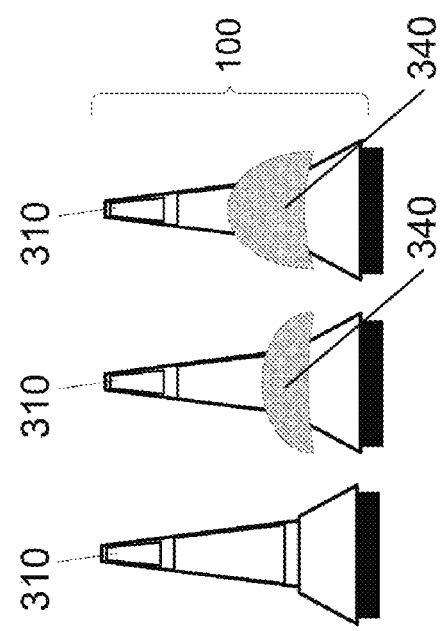
Figure 9B:
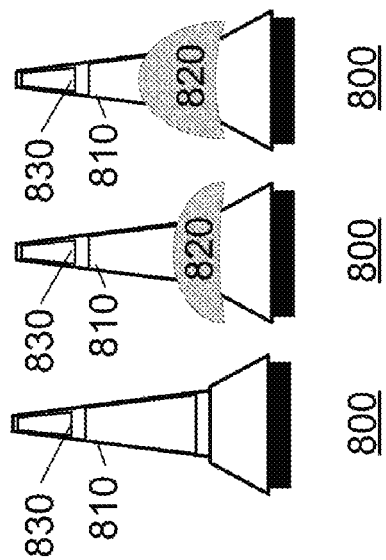
Figure 11:
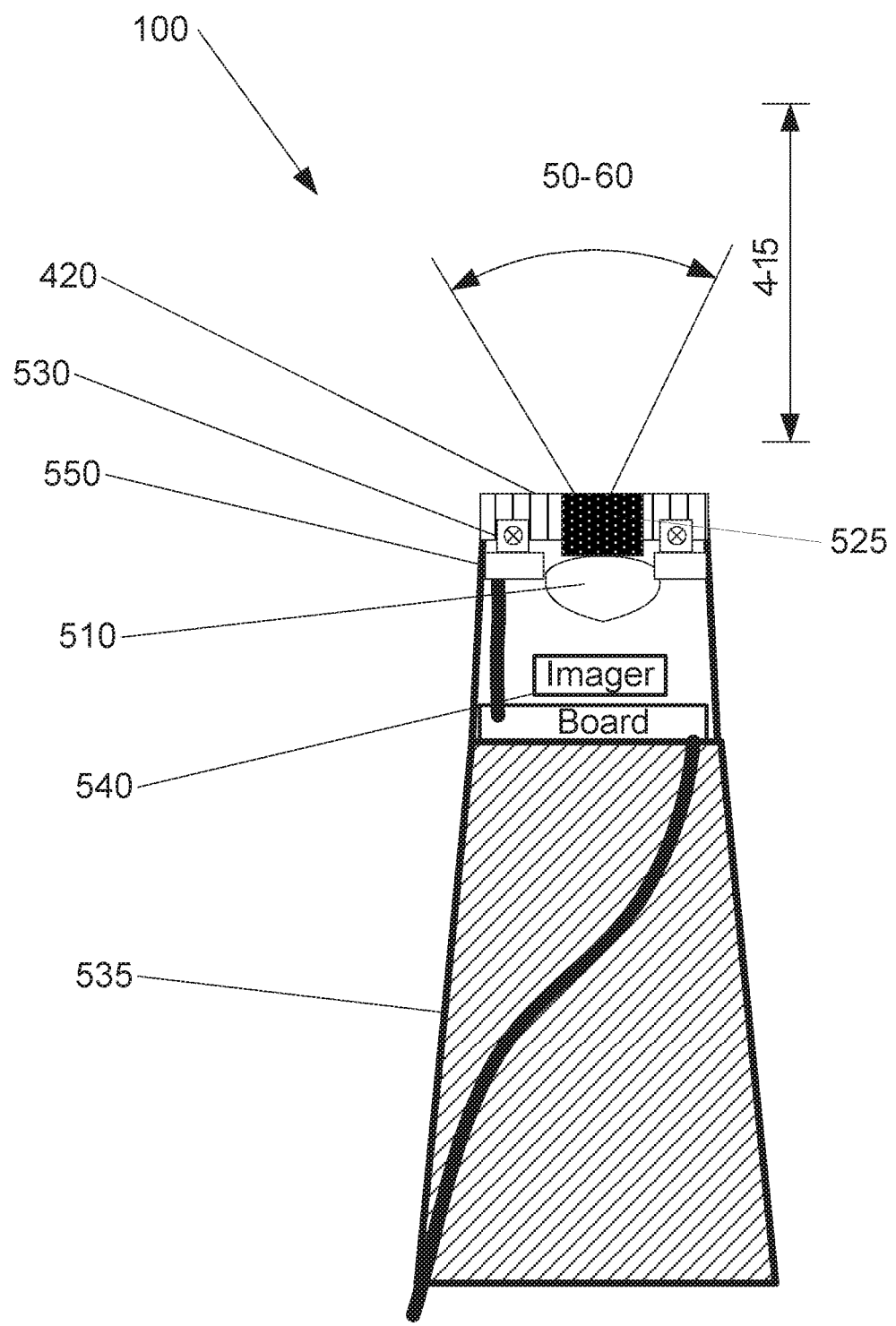
Figure 12:
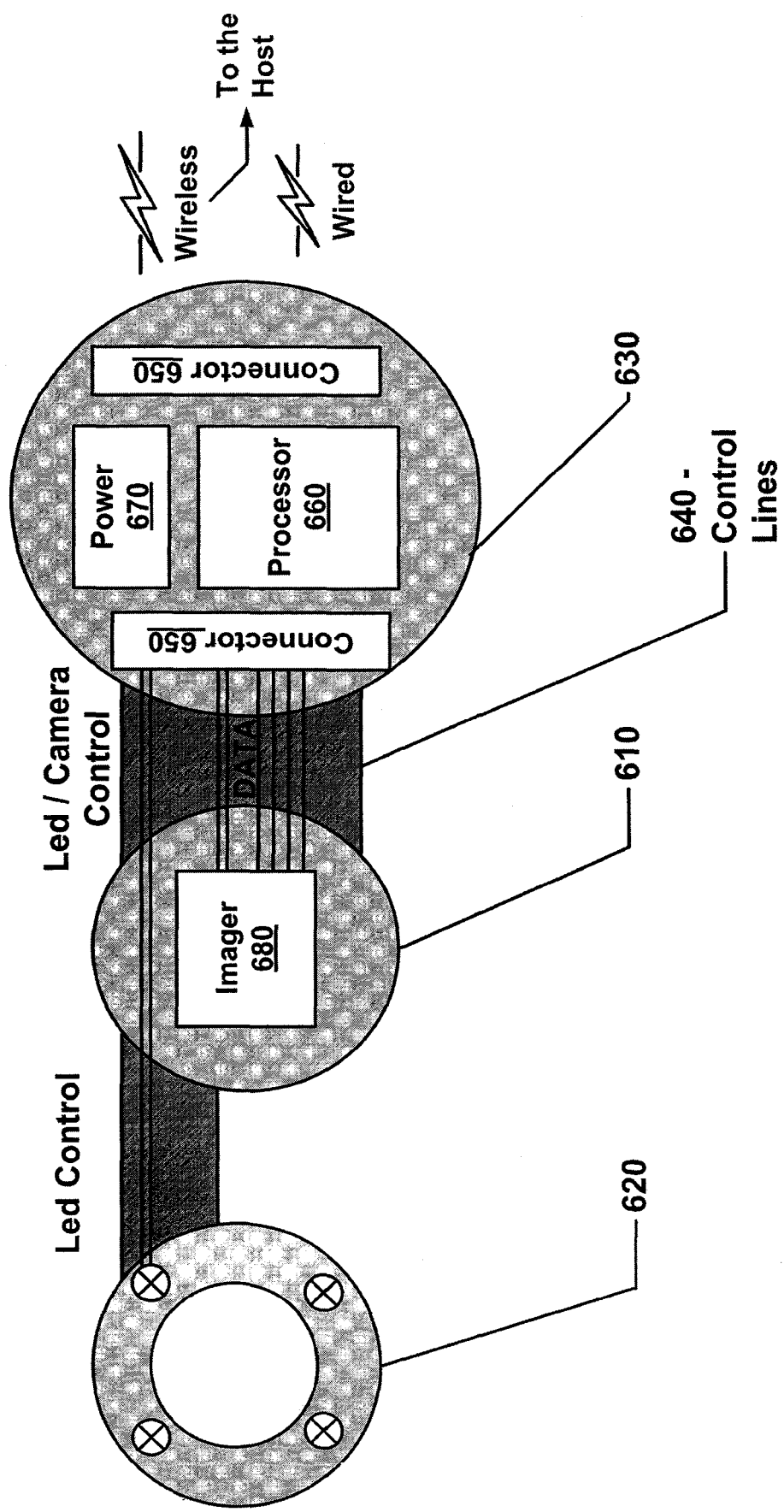
Figure 13:
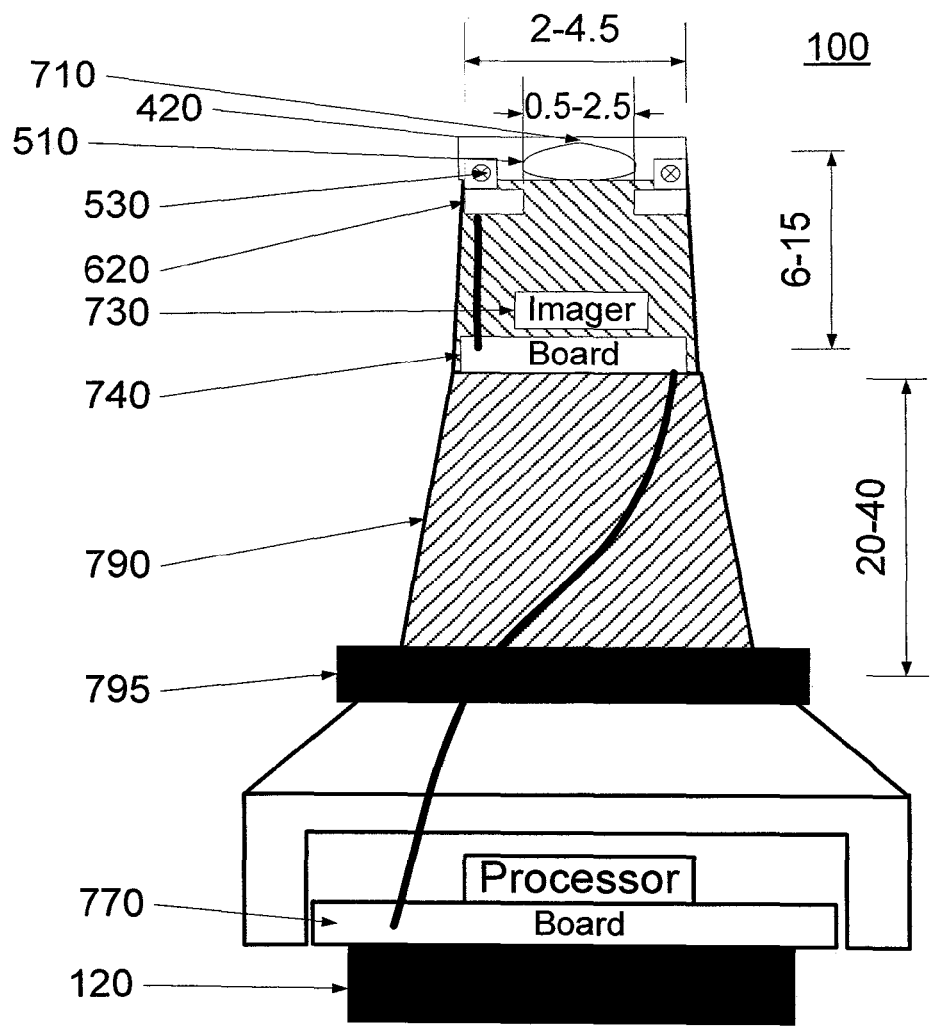
Figure 14:
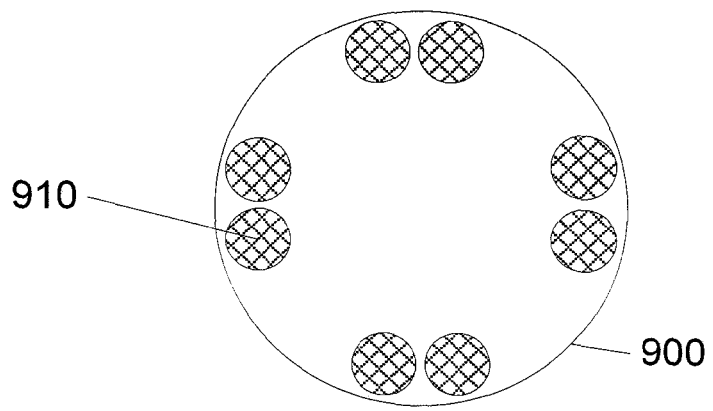
Figure 15:
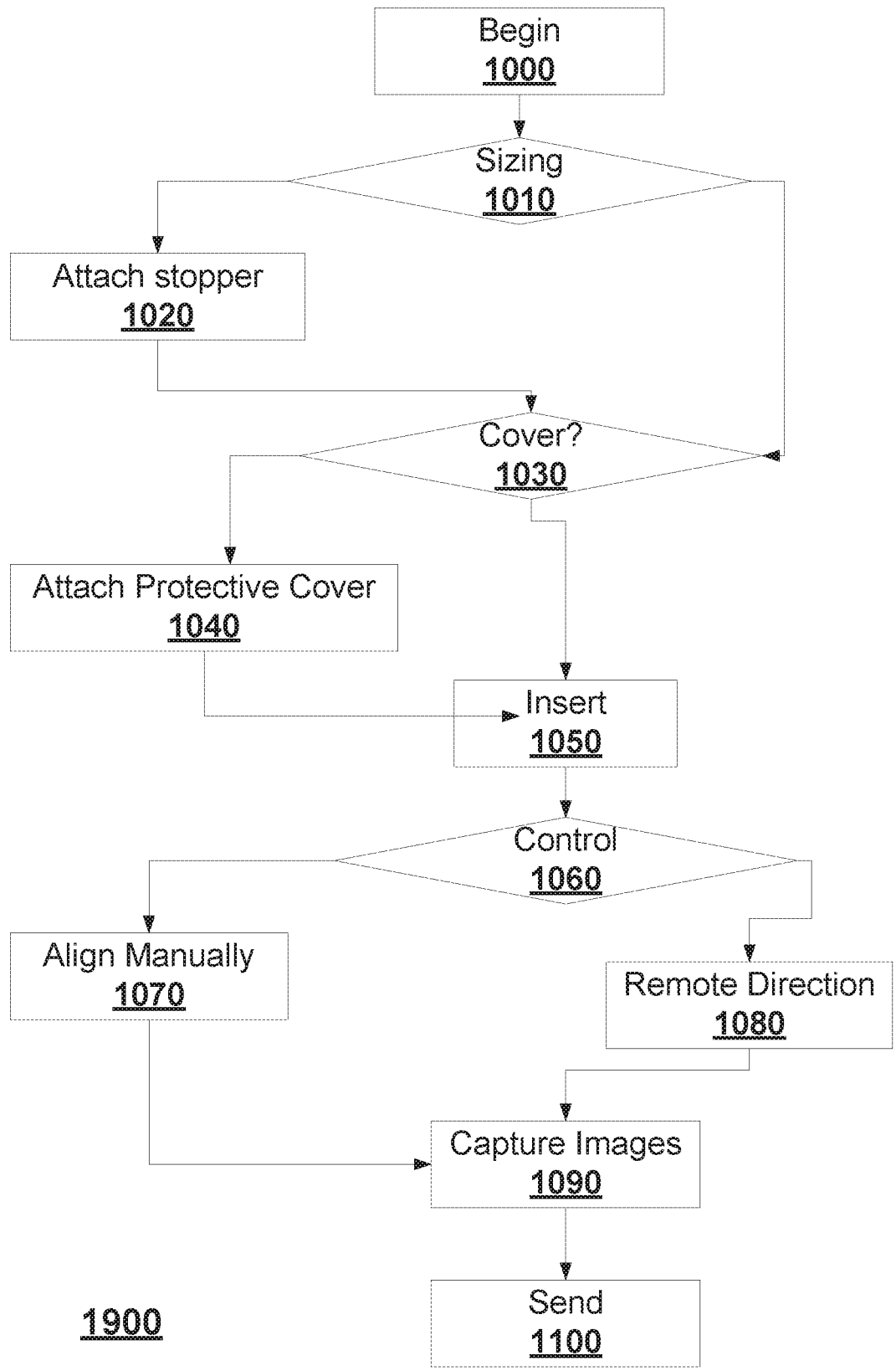

In order to understand the presently disclosed subject matter and to see how it can be carried out in practice, the subject matter will now be described, by way of non-limiting examples only, with reference to the accompanying drawings, in which:

FIGS. 1A, 1B, 1C and 1D are a diagrams illustrating examples of an otoscope, in accordance with the presently disclosed subject matter;

FIG. 2 is a diagram illustrating an example of am otoscope with a plurality of interchangeable stoppers, in accordance with the presently disclosed subject matter;

FIG. 3 is a diagram illustrating an example of an otoscope with a controllable stopper, in accordance with the presently disclosed subject matter;

FIGS. 4A and 4B are a diagrams illustrating examples of an otoscope with a flexible cover, in accordance with the presently disclosed subject matter;

FIG. 5 is an illustrative depiction illustrating an example of a speculum, in accordance with the presently disclosed subject matter;

FIG. 6A is a functional diagram illustrating an example of an image capture system for use in a speculum, in accordance with the presently disclosed subject matter;

FIG. 6B is a functional diagram illustrating an example of an image capture system including external components for use in a speculum, in accordance with the presently disclosed subject matter;

FIG. 7A is a network diagram illustrating an example of a speculum in communication with one or more devices, in accordance with the presently disclosed subject matter;

FIG. 7B is a network diagram illustrating an example of a speculum in a network based communication with one or more devices, in accordance with the presently disclosed subject matter;

FIGS. 8A and 8B are schematic depictions illustrating examples of a speculum with reference to an ear canal, in accordance with the presently disclosed subject matter;

FIGS. 9A and 9B are schematic depiction illustrating examples of a speculum and a limiter with reference to an ear canal, in accordance with the presently disclosed subject matter;

FIGS. 10A through 10E are schematic depiction of examples of a cover for a speculum, in accordance with the presently disclosed subject matter;

FIG. 11 is a schematic depiction illustrating an example of optics in a speculum, in accordance with the presently disclosed subject matter;

FIG. 12 is a schematic depiction illustrating an example of electronic connections in a speculum, in accordance with the presently disclosed subject matter;

FIG. 13 is a schematic depiction illustrating an example of a speculum internal, in accordance with the presently disclosed subject matter;

FIG. 14 is a schematic depiction illustrating an example of a set of connectors for a speculum, in accordance with the presently disclosed subject matter;

FIG. 15 is a flowchart illustrating an example of a method for using a speculum, in accordance with the presently disclosed subject matter; and FIGS. 16A, 16B and 17 are flow charts illustrating examples of a method for intraaural imaging, in accordance with the presently disclosed subject matter.

DETAILED DESCRIPTION

In the following detailed description, numerous specific details are set forth in order to provide a thorough understanding of the methods and apparatus. However, it will be understood by those skilled in the art that the present disclosed subject matter can be practiced without these specific details. In other instances, well-known methods, procedures, and components have not been described in detail so as not to obscure the present disclosed subject matter.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "obtaining", "sending", "receiving", "specifying", "enabling", "selecting", "generating", "transmitting", "extracting", or the like, include action and/or processes of a computer that manipulate and/or transform data into other data, said data represented as physical quantities, e.g. such as electronic quantities, and/or said data representing the physical objects. The term "computer" should be expansively construed to cover any kind of electronic device with data processing capabilities, including, by way of non-limiting examples, a computer-based inspection unit, a computer-based die layout clipping unit and a processor disclosed in the present application.

The terms "coupled" and "connected" and their derived terms are used interchangeably in the specification, and are intended to convey the same meaning within the scope of the present specification.

In some embodiment of the presently disclosed subject matter, an apparatus and/or methods can allow both clinicians as well as non-trained consumer to perform an easy, high quality body imaging and examination while connecting to any standard mobile device or any proprietary medical-quality imaging device, in order to transfer the medical reading to a health professional for review.

FIGS. 1A, 1B, 1C and 1D are a diagrams illustrating examples of otoscope 800, in accordance with the presently disclosed subject matter. Otoscope 800 includes at least flexible speculum 810, stopper 820 and imaging sensor 830 which is located inside flexible speculum 810. Otoscope 800 may be used for obtaining images from inside an ear canal, and especially of the ear drum.

Flexible speculum 810 is operable to be inserted into the ear canal (e.g. as exemplified in FIGS. 8B and 9B). The flexibility of flexible speculum 810 allows alignment of imaging sensor 830 according to a shape of the ear canal (e.g. as exemplified in FIGS. 8B and 9B). That is—flexible speculum 810 (or at least part of it) bends as it is moved through the ear canal, where the bending (also referred to as flexing) results from forces applied on flexible speculum 810 by the walls of the ear canal. Such forces may be applied on the tip of flexible speculum 810 if it is pushed towards the wall of the ear canal (usually at shallow angles), or on any other part of flexible speculum 810, and are forces resulting (at least in part) from the pushing of flexible speculum 810 into the ear canal.

Figure 1B:
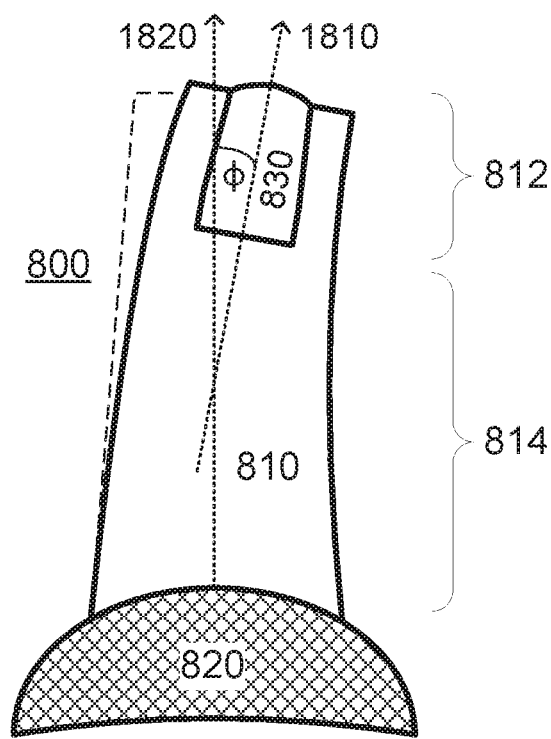
Figure 1C:
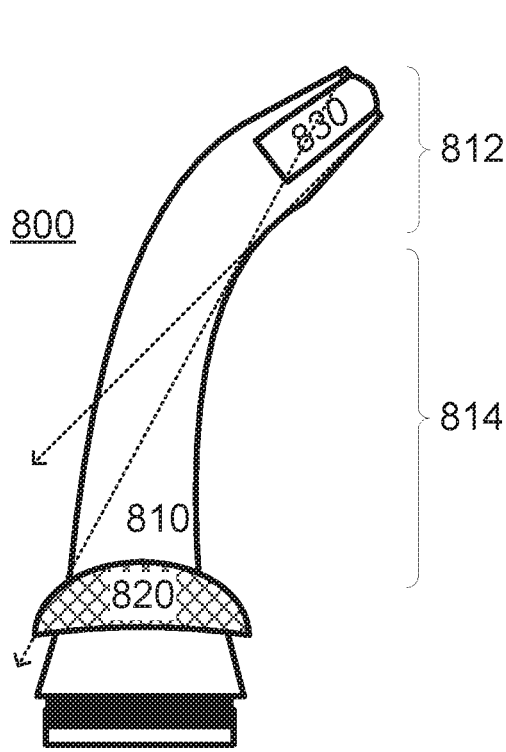

FIG. 1B illustrates a bending of flexible speculum, and the angle (denoted φ) between an optical axis of imaging sensor 830 (denoted axis 1810) and a longitudinal axis of a back part of flexible speculum 810 (denoted axis 1820) define an angle of at least 10 degrees. It is noted that optionally, axis 1810 may be a stationary axis with respect to a portable system to which flexible speculum 810 is connected (if any). Such a system may be, for example, a handle, a smartphone, a propriety handheld diagnostic device (e.g. as manufactured by Tyto Care Inc. of Netanya, Israel), and so on. However, the connection between the base of flexible speculum 810 and such carrying system (if any) may also be flexible.

For ease of reference, tip 812 of flexible speculum 810 is referred to as the front part of the speculum, and the other end of the speculum is referred to as the back of the speculum. The frontmost plane of tip 812 is referred to as the leading plane of flexible speculum 810, as it is the first part of flexible speculum 812 to enter further into the ear canal when otoscope 800 is entered into the ear canal.

These terms of front and back are also applicable to other components of otoscope 810, and are used as a matter of convenience only. The tip of flexible speculum 810, denoted 812, may include parts or all of imaging sensor 830. The length of tip 812 may depend on the components of otoscope 800 which are located inside tip 812. The part between tip 812 and the base of flexible speculum 810 is referred to as the "body" of flexible speculum 810, and is denoted 814.

Optionally, e.g. as discussed below in greater detail, tip 812 and body 814 may have different physical qualities, such as different flexibilities, different strengths, different materials or material compositions, different texture, and so on. For example, flexible speculum 810 may include: a rigid tip 812 (also referred to as inflexible tip) which includes imaging sensor 830, and (b) a flexible part (e.g. the entire body 814 or part thereof) which connects the inflexible tip and a base of the flexible speculum. This way, the bending of flexible speculum 810 when it is inserted into the ear canal happens at the flexible part (e.g. body 814), while tip 812 is sufficiently rigid to prevent any bending, twisting or external forces from harming optical sensor 830 or interfering with its operation. Optionally, there are no flexible parts between optical sensor 830 and a frontmost part of otoscope 800 (and especially a frontmost part of flexible speculum 810).

The terms flexible and inflexible are naturally relative, and depend on the context of operation. The rigidity of rigid tip 812 in the present example is sufficient to prevent bending or twisting of tip 812 to a degree which would harm optical sensor 830 or which would interfere with its operation—when subject to forces resulting from movement of flexible speculum 810 inside the ear canal. The flexibility of the flexible part is such which would allow alignment of the flexible speculum 810 to a shape of the ear canal—when subject to forces resulting from movement of flexible speculum 810 inside the ear canal. For example, the flexible part of flexible speculum 810 may have durability between shore A10 and shore A100.

It is noted that imaging sensor 830 may be located in the front of flexible speculum 810, e.g. as discussed above. For example optionally a distance of imaging sensor 830 from the leading plane (and especially from a frontmost point of flexible speculum 810 which is included in the leading plane) is smaller than a quarter of the distance between stopper 320 and the leading plane.

Imaging sensor 810 is operable to capture an image of the ear drum of the ear canal (i.e. which is located at the end of the ear canal), and optionally, other parts inside the ear as well. Since imaging sensor 810 is located inside flexible speculum 810 which is inserted (at least partly) into the ear canal, and may therefore optionally be operable to capture an image of the eardrum when it is located inside the ear canal.

The angle φ between the optical axis of imaging sensor 830 and the longitudinal axis of the base of the speculum may change during the insertion of flexible speculum 810 deeper into the ear canal. This angle φ may depend on different factors such as the shape of the ear canal in different patients, the depth into which flexible speculum 810 is inserted, and the shape of flexible speculum 810 (or any component of otoscope 800 which comes between the ear canal and flexible speculum 810, such as cover 870 discussed below). For example, during an acquisition of an image of the eardrum (or of another part inside the ear), the angle φ may be between 10 and 30 degrees. It is noted that greater and smaller angles may optionally be reached.

For example, imaging sensor 830 may be operable to capture an image of the eardrum when the optical axis of the imaging sensor and the longitudinal axis of the back part of flexible speculum 810 define an angle of at least 10 degrees. It is noted that in such angles, imaging sensor 830 which is positioned inside flexible speculum 810 receives light rays which cannot reach the base of flexible speculum 810 (corresponding to the location of cameras in widely available prior art otoscopes) without expensive optics.

Optionally, imaging sensor 830 is operable to capture the image of the eardrum when a bending of flexible speculum 810 blocks any line of sight between the tip of flexible speculum 810 and the base of flexible speculum 810. That is, at the moment of capturing the image by imaging sensor 830, all of the straight lines from the tip of flexible speculum 810 which pass inside flexible speculum 810 do not reach the base of flexible speculum 810—and especially do not reach outside the ear canal. A bending of flexible speculum 810 (having a rigid tip 812) in a manner which blocks any line of sight between the tip and the base of flexible speculum 810 is demonstrated in FIG. 1C.

Prior art otoscope often require pulling of the auricle (also referred to as pinna) in order to achieve a line of sight through the speculum, from the eardrum to the eye of the physician or the camera, located outside the ear. The flexibility of flexible speculum 810 enables an easy insertion of flexible speculum 810 into the ear canal, even by an untrained person (e.g. the patient herself, or a family member), and even when the auricle is at its resting position (i.e. it is not pulled by any person or device).

Imaging sensor 830 may optionally be operable to capture the image of the eardrum when the auricle of the ear canal is at its rest position. While not necessarily so, in some cases (e.g. in some patients) the rest position of the auricle is such which does not provide a line of sight to the eardrum from outside the ear canal. Optionally, flexible speculum 810 may be operable to be inserted into the ear canal when the auricle of the ear canal is at its resting position.

In order to prevent excessive insertion of flexible speculum 810 into the ear canal (which may damage the eardrum or other parts of the ear), stopper 820 is connected to flexible speculum 810. Stopper 820 is operable to limit penetration depth of flexible speculum 810 into the ear canal. Stopper 820 is wider than the ear canal, and therefore stopper 820 limits the penetration depth mechanically. Flexible speculum 810 has a longitudinal axis of a back part of flexible speculum 810 (denoted axis 1820 in FIG. 1B). The width of stopper 820 in at least one direction perpendicular to axis 1820 is wider than an opening of the ear canal (i.e. it is wider than its widest dimension). Therefore, stopper 820 cannot enter the ear canal. In addition to the shape of stopper 820 preventing insertion of parts of flexible speculum 810 into the ear canal, other stopping mechanisms may also be implemented by stopper 820. For example, materials from which stopper 820 is made may create friction which prevents (or at least limits or slows) insertion of parts of flexible speculum 810 into the ear canal.

Optionally, otoscope 800 may be usable for imaging inside the ear canals of different patients, having ear canals of different sizes (both depths, widths, curving, and overall shape). Such different ear canals may require different speculums 810 and/or different stoppers 820 to be used, or having the option to adjust the penetration depth permitted by stopper 820. It is noted that the different penetration depths permissible by the interchangeable stoppers 820 and/or by the adjustable stopper 820 may also be used with a single patient—e.g. for different types of physiological measurements.

Optionally, stopper 820 may be mechanically configurable to limit the penetration of the flexible speculum into the ear canal to different depths. This may be implemented, for example, by moving the entire stopper 820 with respect to speculum 810 (and/or with respect to a portable handheld unit to which speculum 810 may optionally be connected, e.g. as exemplified above and below), or by moving parts of stopper 820. Such movements of stopper 820 or of parts thereof may be facilitated by different means known in the art, such as screws, magnets, linear motion drives, and so on.

Optionally, flexible speculum 810 may be detachably connectable to a plurality of different sized stoppers 820. In such case, flexible speculum 810 is connected to different stoppers 820 at different times, thereby managing the different depths permissible for insertion of flexible speculum 810 into the ear canal.

FIG. 2 is a diagram illustrating an example of otoscope 800 with a plurality of interchangeable stoppers 820, in accordance with the presently disclosed subject matter. It is noted that only few shapes of stoppers 820 are illustrated, for the sake of illustration only, and that many other types of stoppers may be used.

FIG. 3 is a diagram illustrating an example of otoscope 800 with a controllable stopper 320 whose position with respect to the imaging sensor 830, to the base of flexible speculum 810 and/or to flexible speculum 810 in general, in accordance with the presently disclosed subject matter. In the illustrated example, stopper 320 may be screwed up and down the body of flexible speculum 810, along a screwing of the body. However, as mentioned above, other techniques of moving stopper 320 while still enabling it to securely stop the movement of flexible speculum 810 inside the ear canal may be implemented.

It is noted that stopper 820 may be a dedicated part whose only (or at least main) functionality is being a stopper, but this is not necessarily so. Any part of otoscope 800 (whether part of flexible speculum 810 or not) may serve as stopper 820—e.g. by being shaped to serve as a stopper. Any part of otoscope 800 may serve as a stopper if it is wider than the ear canal, and this wide part is near enough to the frontmost part of flexible speculum 810, so that it prevent insertion of flexible speculum 810 into the ear canal beyond a certain depth. Especially, stopper 820 must prevent flexible speculum 810 from reaching the eardrum. Optionally, stopper 820 may be implemented by shaping a handle of the otoscope, or a handheld computer which is detachably connected to flexible speculum 810 (e.g. which may include processor 850 and communication unit 890, among other things).

Figure 1D:
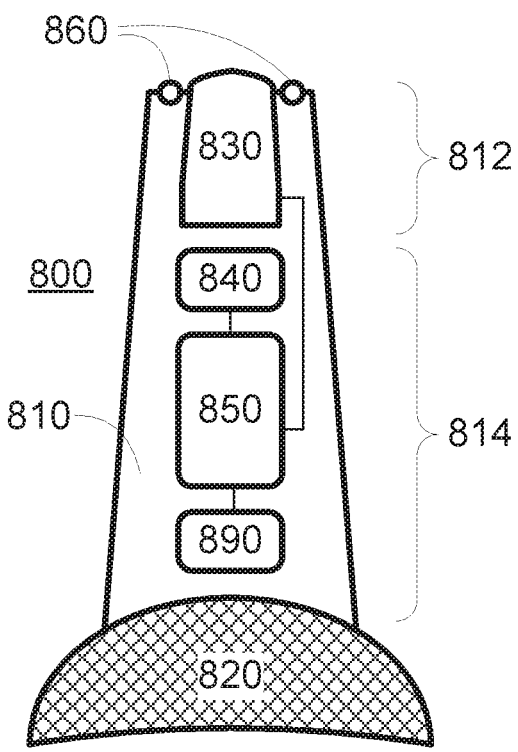

Referring to FIG. 1D, it is noted that optionally, otoscope 800 may include one or more light sources 860 (e.g. light emitting diodes—LEDs—incandescent light bulb, etc.) for illuminating inside the ear canal, wherein at least part of the light collected by imaging sensor 830 for generating the image of the ear drum is light from the one or more light sources which is reflected from the interior of the ear.

Optionally, otoscope 800 may include processor 850, which is operable to control one or more components of otoscope 800. Such controlled components may include, for example, imaging sensor 830, lights 860, physiological sensor 840, power supply unit (not illustrated), wired communication unit (not illustrated), wireless communication unit 890, and so on. Optionally, otoscope 800 may include a processor 850, which is operable to process data arriving from one or more components of otoscope 800. Such components may include, for example, imaging sensor 830, physiological sensor 840, wired communication unit (not illustrated), wireless communication unit (not illustrated), and so on.

Optionally, otoscope 800 may include communication unit 890. Communication unit 890 may be located inside flexible speculum 810, but this is not necessarily so. Communication unit 890 may use wireless communication (e.g. Wi-Fi, Bluetooth, etc.), wired communication (e.g. USB, serial bus) or a combination of both. Communication unit 890 may be used for communication with other components of otoscope 800 (e.g. with a control unit located at a detachable handle or medical device to which the flexible speculum 810 may be connected), or to a remote unit (e.g. another computer, a server, and so on). Communication unit 890 may be used for transmission of data generated by otoscope 800 (e.g. imaging sensor 830, processor 850), and/or for reception of data (e.g. instructions, error correction communication, and so on).

Optionally, otoscope 800 may include one or more physiological sensors 840 positioned inside flexible speculum 810. Different kinds of physiological sensors may be implemented as physiological sensor 840. For example, physiological sensor 840 may be operable to measure a nonvisual physiological parameter inside the ear canal. For example, the one or more physiological sensors 840 may measure any one or more of the following types of nonvisual physiological parameters—body temperature, blood pressure, blood saturation, electrocardiogram (ECG) measurements, audio signals, ultrasound signals, acoustic measurements, body tissue electrical resistance, hardness of body tissues, and so on.

FIGS. 4A and 4B are a diagrams illustrating examples of otoscope 800 with a flexible cover 870, in accordance with the presently disclosed subject matter. Optionally, otoscope 800 may include flexible cover 870 for covering flexible speculum 810. Flexible cover 870 may be used, for example, for hygienic reasons—e.g. if otoscope 800 is used by different people, or if it is used in a time of sickness. It is noted that flexible cover 870 may touch flexible speculum 810 during the time of operation, and that the distance between the cover and the speculum in FIGS. 4A and 4B is exaggerated for reasons of clarity of the illustration. As demonstrated in the example of FIG. 4B, the flexibility of flexible cover 870 may be such which allows alignment of imaging sensor 830 and/or of flexible speculum 810 and/or of flexible cover 870—according to a shape of the ear canal. That is—flexible cover 870 (or at least part of it) may bend as it is moved through the ear canal, where the bending (also referred to as flexing) results from forces applied on flexible cover 870 by flexible speculum 810 and by the walls of the ear canal.

Flexible cover 870 may include an optical tip 880 (not to be confused with tip 812 of flexible speculum 810), which is operable to transfer light from the eardrum to imaging sensor 830. Optical tip 880 may be fully transparent or partly transparent.

It is noted that optionally, flexible cover 870 may be replaceable. Optionally, flexible cover 870 may be disposable. Otoscope 800 may include a connection (not illustrated) for detachably connecting flexible cover 870 and flexible speculum 810. Such a connection may be a mechanical connection (e.g. hooks and hoops connection), chemical connection (e.g. glue, etc.). In some implementations, the connection between flexible cover 870 and flexible speculum 810 may be achieved by friction.

Additional information regarding flexible cover 870 is offered below, e.g. with respect to FIGS. 10A through 10E.

FIG. 5 is an illustrative depiction of speculum 100, in accordance with the presently disclosed subject matter. Speculum 100 may serve as flexible speculum 810, as long as its flexibility allows alignment of imaging sensor 830 according to the shape of the ear canal. Therefore, every detail provided below with respect to speculum 100 is applicable to flexible speculum 810, with the condition that the flexibility of the speculum allows alignment of imaging sensor 830 according to the shape of the ear canal.

A speculum 100, for example as described herein and below, can be flexible and/or rigid, partially rigid, partially flexible and/or otherwise constructed. Speculum 100 can be sized, shaped and/or otherwise configured for proper, optimal, near optimal, sufficient, medically necessary, or other interface with various body parts and cavities. These body parts and cavities can include external ear canal, mouth, throat and other cavities or parts. Speculum 100 can be configured to allow the capturing of digital video or still images of the relevant orifice, organ and/or other body part or cavity.

Optionally, speculum 100 can include a speculum housing 110. Speculum housing 110 can be flexible and/or rigid design. Optionally, a flexible housing can be made of a flexible medical grade elastomer, including rubber, silicon and/or other elastomers. Optionally, a rigid housing, and/or portion thereof can be made of a rigid medical grade elastomer, including for example, moldable plastic material, such as polypropylene, and other rigid medical grade elastomers.

Optionally, speculum 100 can include or be configured to use an adaptor. Optionally a size adapter, the size adapter configurable to fit on the speculum to allow length and width changes to the diameter and length of the speculum portion which can safely or otherwise enter the body cavities. This size adaptor can be configured to allow easy and safe usage on animals, infants, children & adults, using the same speculum. With respect to its possible use as flexible speculum 810, the size adapter may incorporate some of the functionalities and/or structure of stopper 820, but other techniques of adapting may be used. For example, the width of the speculum may be affected by stretching its base over differently sized connectors of an otoscope body (external to the ear canal), if any Optionally, speculum 100 can include or be configured to use a cover, for example, a protective cover. Optionally, the protective cover can be elastic or rigid, to be attached to the speculum housing to allow sanitary usage. The optional cover of Speculum 100 (also referred to as protective cover 420, e.g. in reference to FIG. 10B) may serve as flexible cover 870, as long as it is flexible. Therefore, every detail provided below with respect to the cover of speculum 100 (e.g. cover 420) is applicable to flexible cover 870, mutatis mutandis.

Optionally, speculum 100 can include or be configured to use a protrusion or other inconsistency and/or irregularity in speculum housing 110. The protrusion can optionally be a lip for use, or configurable for use in maintaining the position of the protective cover with reference to speculum 100. Such a protrusion or inconsistency may serve as the connection of the cover to the speculum, or to another part of the otoscope.

Speculum 100 can be configured to be used in a medical environment for use in the examination and/or diagnosis of a medical, health-related condition, or other conditions. Optionally, speculum 100 can be configured to be used in a home environment and for use in providing quantitative and/or qualitative data and/or imagery for use in a third party's examination and/or diagnosis of a medical, health-related and/or other condition.

Optionally, speculum 100 is configured or configurable for use in children. Optionally, speculum 100 is configured for use in adults. Optionally, speculum 100 can be configured for use in animals and in other veterinary related settings.

Optionally, speculum 100 can be configured to be used as a diagnostic tool in a clinical and/or quasi medical environment. Optionally, speculum 100 can be configured to be used for telemedicine. Speculum 100 can be configured to be used as a direct to consumer tool for a non-medical and/or recreational use. Optionally, speculum 100 can be used for non-medically related uses.

Optionally, speculum 100 can be configured for use in viewing one or more parts of an ear. Optionally, speculum 100 can be configured for use in viewing one or more other body parts. Optionally, speculum 100 can be configured for use in viewing one or more human and/or animal orifices, real and/or simulated.

Optionally, speculum 100 can be an attachment to a proprietary device. Optionally, speculum 100 can connect via a wired and/or wireless connection to one or more devices, wherein the one or more devices can include a proprietary device, a portable computing device, and/or other devices. Optionally speculum 100 can be a component within a training system, the speculum configured to simulate a medical, veterinary or other exam, and/or a component thereof. For example, the device may be a portable physiological measurement devices, e.g. as produced by Tytocare LTD of Netanya, Israel.

Optionally, speculum 100 can be in other communications with one or more devices, wherein the one or more devices can include a device providing an internet connection. The one or more devices can include a portable computing device including a smartphone, tablet computer, phablet and or/or other devices. Optionally, speculum 100 may connect physically, wired, or wirelessly to a medical device and/or medical-like medical-quality consumer medical device, and/ or other devices. Optionally, speculum 100 is configured to be used in conjunction with one or more devices. Optionally, speculum 10 is configured to be a standalone device.

FIG. 6A is a functional diagram illustrating an example of an image capture system 10 for use in a speculum, in accordance with the presently disclosed subject matter. It is noted that optionally, system 10 may be incorporated into speculum 100. Optionally, system 10 may be incorporated into flexible speculum 810. In such case, camera 60 of system 10 may serve as imaging sensor 830, processor 30 may serve as processor 850, and so on.

Speculum 100 (as well as flexible speculum 810) may include image capture system 10 for electronically capturing and/or processing images using the respective speculum. Image capture system 10 may include one or more light sources 20. The one or more light sources 20 can include one or more LEDs. The one or more light sources can be configurable to provide light across a spectrum of wavelengths, including, optionally, ultraviolet, infrared, and other wavelengths. The one or more light sources 20 can be positioned at one or more locations in speculum 100. Optionally, light sources 20 can be positioned such that the light from light sources 20 provides a direct path, e.g., line of sight, with a target to be viewed by a user of speculum 100, for example, an eardrum.

Optionally, light sources 20 can include and/or interact with one or more illumination modules. The illumination modules can include multiple LEDs, the multiple LEDs can be controlled separately.

Optionally, image capture system 10 may include one or more processors 30. Processor 30 can be connected via wired or wireless communication methods with other components of speculum 10. Processor 30 can be located within speculum 100 or it can be in communication with components with speculum 100 remotely. Optionally, a first processor 30 can be in speculum 100 physically and a second processor 30 can be in communication with components of speculum 100 but physically outside speculum 100.

Image capture system 10 includes optics 40. Optics 40 can include mirrors, lenses, fiber (e.g. optical fiber), and/or other components of optic systems. Optics 40 can be housed, located and/or otherwise associated with one or more areas of speculum 100. Optionally, optics 40 can include optical lens. Optical lenses can be built into the speculum and/or can be attached to a distal end (i.e., the end configured to be closest to the eardrum during an ear inspection) of the speculum and may be fitted to adjust the specific optical requirements of the specific organ being examined. Optics 40 can be configured to allow for specific range of depth of field or field of view, and/or light or color filtering.

Image capture system 10 can include communication modules that can be configured to provide connections 50. Connections 50 can include devices and/or items to provide physical and/or wireless connections to one or more internal and/or external devices. Connections 50 can include power and/or communication connections, and/or other connections with other components. Connections 50 can include, for example, Universal Serial Bus (USB) connections, Ethernet connections, and/or proprietary connections methods.

Optionally, a communication module may be implemented in system 10, and can be configured to connect image capture system 10 to a mobile device, computer and/or a proprietary medical device, e.g., a host. Optionally, a wired connection can include a standard connector and cable, for example USB, Mini/Micro USB, and/or other proprietary or non-proprietary connectors.

Optionally, a wired connection can include one or more proprietary connectors. The one or more proprietary connectors can be attached to a $3^{rd}$ party medical device or to a generic connector which is physically attached to a mobile device, and/or other devices.

Optionally, a wireless connection can include connections that are configured to use protocols such as Bluetooth, Wi-Fi or any other standard wireless protocols. Optionally, a wireless connection can be configured to use a proprietary, non-standard or other wireless protocol.

Image capture system 10 can include one or more sensors, including, optionally, camera 60. Camera 60 can be configured for the collection of images, video and/or both. Camera 60 can be in direct and/or indirect communication with other components of image capture system 10 and/or other systems. A camera can include a digital camera sensor, including Complementary metal-oxide-semiconductor (CMOS) or charge-coupled device (CCD) based sensor or other sensors.

Image capture system 10 can include a power source 70. Power source 70 can be directly and/or indirectly connected to image capture system 10. Power source can be configurable to provide an appropriate amount of power necessary for the functioning of speculum 100 and/or system 100 (and to the components of the respective speculum/system).

FIG. 6B is functional diagram illustrating an example of image capture system 10 and external devices 80 for use in a speculum, in accordance with the presently disclosed subject matter.

In addition to components of image capture system 10 described above, image capture system 10 can also include one or more external devices 80. The devices can be configurable to interface with other components of image capture system 10. External devices 80 can provide, memory, communication, processing power, power, interfaces, and/or other services for speculum 10. External devices 80 can be proprietary and/or standard devices. The detailed description of image capture system 10, and components thereof, provided above with reference to FIG. 6A is equally applicable here with reference to FIG. 6B, with appropriate modification where needed.

FIG. 7A is a schematic network diagram illustrating an example of a speculum in communication with one or more devices, in accordance with the presently disclosed subject matter. The speculum of FIG. 7A may be speculum 100 or flexible speculum 810. In the following discussion, the example of speculum 100 is used, but as mentioned above— it may apply, mutatis mutandis, to flexible speculum 810.

A speculum, for example, speculum 100 described herein, can have one or a plurality of different connectors 120, e.g., expansion connectors. The expansion connectors 120 can be configured for one or more connections, including, data, power, and other connections. Connectors 120 can be part of a solid body of the speculum, and/or configured to be attachable, detachable in a permanent, semi-permanent or temporary fashion.

Optionally, a connector 120 can be configured to transmit stills and/or video information over a USB cable and can provide a USB standard camera-like communication to PC/Tablet or Mobile device and/or other computers and/or other devices, 130.

Optionally, a connector 120 can be configured to transmit stills and/or video information over wireless connection. Optionally, the wireless connection can provide standard camera-like communication to a local host 170. The local host can be a computing device, including a laptop or mobile device, etc. Optionally the local host can be a PC/Tablet or Mobile device and/or other devices, such as device 130.

Optionally, a connector 120 can be a proprietary connector that implements connection to an external and/or connectable device 150, e.g. a proprietary device. Optionally, information collected via and/or through speculum 100 can be transmitted over Wi-Fi, and/or other connections to a local host or over the internet.

FIG. 7B is a schematic network diagram illustrating an example of a speculum in internet based communication with one or more devices, in accordance with the presently disclosed subject matter. The speculum of FIG. 7B may be speculum 100 or flexible speculum 810. In the following discussion, the example of speculum 100 is used, but as mentioned above—it may apply, mutatis mutandis, to flexible speculum 810.

Optionally, the currently disclosed subject matter, a system for using a speculum, including for example, speculum 100 described herein can include one or more components.

Optionally, one or more internet gateways 180, for example, a home router/mobile provider or any other device can be connected via a wired and/or wireless connection, directly and/or indirectly to speculum 100.

Optionally, a proprietary device 190 can connect to the gateway 180 using a wireless connection. Optionally, a computing device such as for example a personal computer 200 can act as a local host and can also can access internet using a wired or wireless connection.

Optionally, a portable computing device 210, e.g., a tablet computer or a smartphone can access the local router or use mobile internet provider to communicate with speculum 100 and/or other devices.

When accessed by one or more of the devices described herein, internet gateway 180 transmits can be configured to transfer via one or more internet protocols, information to a third party, for example a local Doctor Station 220 or/and to a third party, commercial and/or proprietary server 230, and/or processor.

FIGS. 8A and 8B are schematic depictions illustrating examples of speculum with reference to an ear canal, in accordance with the presently disclosed subject matter.

Optionally, speculum 100 may include a tip 305 and a body 320. Tip 305 can be rigid, semi-rigid, or flexible. It is noted that tip 305 corresponds to tip 812, and that body 320 corresponds to body 814—where applicable (i.e. when the flexibilities and hardness of these components match to those of flexible speculum 810). Body 320 can be rigid, semi-rigid, or flexible. Body 320 can be of differing lengths. Optionally, body 320 can be made of a medical approved material, for example one or more silicon or silicon-like materials. Some or all of body 320 can have an elasticity factor ranges from shore A10 to shore A90. This elasticity factor is defined in standard ASTM D2240 and could be measured by shore hardness measurement instrument. Elasticity factors of shore A10 to shore A50 can allow a tip optical axis inclination by angles between 0-45 degrees. Manufacturing is done by preferably by thermoforming, from a material such as polypropylene, polyethylene, polystyrene, or other similar material which has relatively low hardness.

Optionally, at least one of tip 305 or body 320 includes an imaging module 310. Imaging module 310 can optionally include some or all components of image capture system 10, and at least a light source and one or more optical components, as described for example, above with reference to FIGS. 6A-7B. Optionally, imaging module 310 can reside elsewhere with regard to other components and modules within speculum 100. Imaging module 310 can interact wirelessly and/or via a hardwired connection with one or more other components and/or modules of speculum 100.

Optionally, some or all of speculum 100 can be covered in one or more medical grade materials, including, for example, a silicon medical grade defined for biocompatibility. Optionally, the tear strength of these materials can be from 5.0 to 15 kN/m, for example, 9.8 kN/m.

Optionally, connector 120 can contain some, all or parts of control and communication circuitry, and/or other circuitry (e.g. processor 30 or parts thereof, processor 850 or parts thereof).

Optionally, given that different ear canals properties can be found in different patients, and among different age groups, speculum 100 can be configured such that the insertion of speculum 100 into an ear canal provides a good view on the ear drum for a wide range of distinct and/or diverse ear canal properties. Optionally, flexibility of speculum 100 can be configured (or otherwise determined or selected) to allow the alignment of imaging component 310 according to the ear canal shape.

FIGS. 9A and 9B are schematic depictions illustrating examples of a speculum and a limiter (also referred to as "stopper") with reference to an ear canal, in accordance with the presently disclosed subject matter. Stopper 340 can correspond to stopper 820, and details regarding stopper 340 may be implemented for stopper 820, mutatis mutandis.

The length and width/diameter of a human and/or animal ear canal varies with species, patient and age, among other factors. In some human infants the length of the ear canal can be short as 15 mm and the diameter can be small as 2 mm while elderly people may have length up to 35 mm and diameter up to 15 mm.

In order to use the same speculum for all different types and sizes of ears, certain design of speculum can use the narrowest possible diameter and the longest length of speculum that will fit both the biggest ears in diameter and length as well as the smallest ear in diameter and length.

In order to limit penetration depth of the speculum certain limiter/stopper is mounted for safety and/or other purposes. The application of a protection stopper can depend on factors such as age, gender and other patient parameters. Protective stopper 340 is configurable to limit speculum 100 penetration. Protective stopper 340 can be one of many iterations, sizes, depths and/or other characteristics, wherein a user can choose to use a particular protective stopper 340 given factors and/or characteristics of an ear canal.

Optionally, speculum 100 could have multiple configurations. In a first configuration, depicted on the left side of the FIG. 9A, speculum 100 could be configured to be used without protective stopper 340.

In a second configuration, depicted to the immediate right of the first configuration, a protective stopper, configurable for use on longer ear canals, for example in teens and adults, e.g., protective stopper 340, can be used in conjunction with the speculum.

In a third configuration, depicted to the immediate right of the second configuration, protective stopper, configurable for use on shorter ear canals, for example in infants and children, e.g., a different sized protective stopper 340, can be used in conjunction with the speculum.

Optionally, protective stoppers 340 can provide a range of depth that the speculum can travel within the ear canal. Optionally, a protective stopper can be configured mechanically or otherwise to achieve a particular depth or depth range within the ear canal. Optionally, protective stoppers can be made of a flexible material. Optionally, protective stopper 340 can be made of an inflexible material. Optionally, protective stopper 340 can be configured to provide a cushion against one or more parts of the ear. Optionally, protective stopper 340 can be configured to provide warning, for example, audio, haptic or otherwise regarding the depth of the speculum within the ear canal.

A protective can coupled to the speculum and the speculum inserted into the ear canal as depicted on the far right of FIGS. 9A and 9B. Optionally, the protective stopper can be automatically detected by the speculum electronics and provide additional levels of safety. The protective stopper could be attached to the speculum body using a connector or other connection means. In some examples protective stopper 340 can be coupled to speculum 100 through two or more means.

FIGS. 10A through 10E are schematic depiction of examples of a cover for a speculum, in accordance with the presently disclosed subject matter. The cover discussed with respect to FIGS. 10A-10E (also referred to as protective cover 420, e.g. in reference to FIG. 10B) may serve as flexible cover 870, as long as it is flexible. Therefore, every detail provided below with respect to the cover of FIGS. 10A-10E (e.g. cover 420) is applicable to flexible cover 870, mutatis mutandis.

Optionally a protective cover can be configured to encase speculum 100 and protective stopper 340. Optionally a protective cover can be configured to encase speculum 100 and not protective stopper 340. Optionally protective stopper can be reusable. Optionally protective stopper 340 can be disposable. Optionally the protective cover can be reusable. Optionally the protective cover can be disposable.

Optionally, a speculum, for example, speculum 100 and/or flexible speculum 810, could have multiple configurations. Optionally, the speculum can have at least three configurations.

Optionally, speculum 100, as depicted, for example in FIG. 10A can be configured such that it has no protective cover. Optionally, speculum used in home and/or noncommercially and/or public settings may be usable without a cover. Optionally, speculum 100 can be configured to be used with a hygienic and/or other sterilization method or technique.

Protective cover 420, as depicted, for example, in FIG. 10B can be flexible, rigid and/or semi rigid. Optionally, protective cover can be flexible with a rigid tip 430. Optionally, rigid tip 430 can have optical qualities. Protective cover 420 can be made from one or more materials, including, for example medical grade materials. Optionally, a flexible rubber with medical grade properties can have similar characteristics to condoms.

Optionally, speculum 100 can be configured such that a protective cover 420 can be configured for use with one or more individuals. Protective cover can be a one-size fits all. Optionally different size protective covers can fit different, and/or corresponding sized speculums 100.

Protective cover 420 can include transparency features that allow one or more portions of speculum 100 to be visible through cover 420. Optionally, optic components of speculum 100, for example optical components described above, are visible through cover 420 (i.e. allow transmission of visible light through cover 420). Optionally, optic components of speculum 100, for example optical components described above, are transparent and/or semi-transparent, allowing passage of light in an amount at least sufficient to the generation of the image of the ear drum.

Optionally the material for cover 420 can be chosen from materials that provide visibility through the cover, the visibility through the cover, sufficient, nearly sufficient or otherwise capable of allowing the optical components to function as configured, designed or otherwise function while cover 420 is on speculum 100. Optionally, cover 420 can include a combination of materials wherein some material are non-transparent, semi-transparent or otherwise not wholly transparent and some materials are transparent, or semi-transparent. Optionally the combination of materials can provide a cover that includes, a rigid transparent tip 430 that provides a covering or a partial covering of a camera and/or other optical components of speculum 100 and a flexible non-transparent and/or less transparent cover than the cover of the tip. This non transparent cover can be of a flexible material. Optionally the entire cover can be flexible, including the tip. Optionally the entire cover can be rigid, including components not at the tip. Optionally, a cover 420 can cover only a portion of speculum 100. Optionally the portion not covered of speculum 100 can include the optics, camera and/or other components.

Optionally, cover 420 can be combined with a functional component, for example in one piece or in a combination of pieces that can be attached and detached.

As depicted, for example, in FIG. 10E, optionally cover 420 contains a rigid tip 430 which has optical quality and manufactured using method 455 as described above and as depicted in FIG. 10D.

Flexible protective skin 480 can be configured to have rubber like quality that can be put on the speculum module. A semi rigid stopper 490 and an integrated part of the flexible part. A connecting element 495 like a rubber strip which could be attached to the speculum and prevent from falling off.

The speculum (e.g. 100, 800) may generate certain amount of heat, especially during its operation. This heat may be generated, for example, through the operation of the camera and/or lights therein. Optionally, wires, conduits, and/or other methods can be configured to evenly spread this generated heat. Possibly, additional heat may be generated bay other elements. This locally generated temperature creates a pleasant warm sensation during the insertion process. Other sensations, including, sound, smell, touch, taste and/or one or more other human ascertainable sensations can be applied or generated by the speculum and configurable to make the use the speculum more amenable, pleasant, easier, or different form a speculum not comprising human ascertainable sensations. For example, pleasant music may be played by speakers of the otoscope, and/or soothing instructions or information may be provided.

As depicted, for example in FIG. 10C, optionally, speculum 100 can be configured such that a stiff protective cover 420 can be used. Optionally, stiff protective cover 420 can have opening 445 at distal end 450. A manufacturing process 455, depicted, for example, schematically on the far right of the figure can be configured such that the tip flexible protective cover can include a hot molding, the hot molding configured to result in glass like properties of the tip. The glass like properties configured to facilitate, or provide for, the one or more optical components of speculum 100, for example optics described herein, to focus and capture images.

Optionally, a flexible, rigid, stiff and/or other protective cover can be configured such that is connectable to the speculum using specialized connector or another attachment means, such as a rubber band, raised component, and/or other connection device, component or method, at, near and/or in proximity to a proximate end 460. The connecting of the cover to the speculum may be a direct connection and/or an indirect connection (e.g. via other parts of the otoscope).

Optionally, speculum 100 can be configured such that a flexible, rigid, stiff and/or other protective cover can be securely, semi securely and/or otherwise attached permanently, semi-permanently or temporarily.

Optionally, flexible, rigid, stiff and/or other protective cover can be configurable to be used with other components in addition to speculum 100. Optionally, flexible, rigid, stiff and/or other protective cover can be configurable to be used with other types of speculum. Optionally flexible, rigid, stiff and/or other protective cover can be configured to provide protective properties to speculum 100 and/or other speculums or devices, including, for example, anti-microbial, or medical properties.

FIG. 11 is a schematic depiction illustrating an example of optics in a speculum, in accordance with the presently disclosed subject matter.

A speculum 100 for example, the speculum described herein can be configured such that the optics therein, for example, the optics described herein, can have a focal distance ranging from 4 mm to 15 mm. Optionally, the focal distance can be narrower, broader, longer or shorter. Speculum 100 can be configured such that it includes optics providing for object resolution below 0.1 mm. Optionally, speculum 100 can be configured such that the optics are changeable, upgradeable, digitally and/or manually manipulatable.

Optics in speculum 100 can optionally include, a lens 510. Lens 510 can be made of a glass, plastic and/or other material configurable to allow sufficient light to pass through. Lens 510 can be in contact with or can be configured within speculum 100 to be near a protective cover 420. Protective cover can be made of plastic, glass and or other materials configurable to allow sufficient light to pass through. Protective cover can be optionally removable and/or a component configured to be permanently, semi-permanently or temporarily attached to speculum 100. Speculum 100 can optionally include an object configured to act as a light diffuser. Optionally, protective cover 420 can act as a light diffuser. Lens 510 can have a diameter in the range of 0.5-2.5 mm Optionally, protective cover 420 (or at least parts thereof, such as its optical tip) can be configured to have the properties of a light diffuser. Optionally, protective cover 420 can be configured to diffuse light emanating from a light source, for example an LED light 530. Optionally, there can be more than one LED light source. Optionally, speculum 100 can include one or more light sources such as a laser and/or other light source.

Speculum 100 can include a transparent window 525 for imaging. Optionally, lens 510 can be configured to transfer and/or refract light which is used in the generation of an image on a sensor, for example a chip 540 configurable to be used in image capturing, e.g. a CMOS or a CCD chip.

Optionally, LED lights 530 can be arranged in a particular pattern, e.g., a circular pattern and/or other geometric symmetrical or non-symmetrical pattern. Led lights 530 can be configured to provide illumination for imaging. Optionally, LED lights 530 are located on, attached to, and/or otherwise coupled to an LED board 550

Optionally, LED lights 530 can be configured to provide 100-200 lux of light. Optionally, LED lights 530 can be configurable to provide a variable amount of light, the variable amount of light can be dependent on conditions of a cavity, battery power, and/or other considerations. The controlling of the amount of light may be executed by processor (e.g. 30, 850). Optionally, LED lights 530 can be configured to provide a sufficient amount of light to sense, view and/or capture an image of one or more objects, the objects in some configurations ranging in size from 1 mm×1 mm to 15 mm×15 mm, for example, 10 mm×10 mm objects, at distance of between 4 mm and 30 mm, e.g., 15 mm, with a minimal SNR (Signal to Noise Ratio) of 10. Optionally, LED lights 530 and/or other lights can be configured to provide infrared, ultraviolet and/or other wavelengths of light. The infrared, ultraviolet and/or other wavelengths of light may optionally be configured, e.g. to allow for better readings.

LED lights 530, chip 540, and/or other components can be connected directly and/or indirectly to processors, power sources and or other components of speculum 500.

Speculum 100 can be covered in a protective material 535, for example, silicon and/or other medical grade, or non-medical grade materials.

FIG. 12 is a schematic depiction illustration an example of electronic connections in a speculum, in accordance with the presently disclosed subject matter. The electronic connections discussed with respect to FIG. 12 (and exemplified in FIG. 12) may be implemented in speculum 100 and in speculum 800. Components of the same name or implied functionalities may correspond to those of the respective speculum. For example, imager 680 can correspond to imaging sensor 830, processor 660 can correspond to processor 850, and so on.

Optionally, a speculum 100 (or 800) can include a Camera/Imager electrical board 610 for controlling and providing communication and/or memory related to a camera and/or image sensor. Speculum 100 includes LED board 620 for controlling LEDs, these boards can be connected to speculum control board 630.

Optionally, an examination image sensor can be located on imager board 610 and connects to a control board 630 via an interface chip using, for example, mobile-based MIPI (Mobile Industry Processor Interface) interfaces and/or parallel data interface, as well as sensors and dedicated I2C channel, and/or via other means.

Control board 630 can be manufactured with several options to support different host connection types including, wired and/or wireless. Optionally, a wired connection can include a USB interface chip and I²C (Inter-Integrated Circuit) interface and/or additional control lines to connect to a host. Optionally, a wireless connection can include a power source, such as a battery, Wi-Fi like chip and/or a processing component configurable to compress and send image data over Wi-Fi or USB.

Optionally, LED board 620 for controlling LEDs is connected to a number of LEDs, for example, 4 LEDs. Optionally, an LED driver located on Control Board 630 can be configured to support adjustable illumination power for each LED jointly and/or separately.

Optionally, the LEDs can be driven by dedicated LED driver. The dedicated LED driver can be located on the Control Board 630 Optionally, control Board 630 can include control lines 640 that can be configured to be subjected to bending.

Speculum 100 can include one or more of any of the following units: imager 680, a processor 660, connectors 650, and power supply 670.

FIG. 13 is a schematic depiction illustrating an example of a speculum, in accordance with the presently disclosed subject matter. The speculum of FIG. 13 may be speculum 100 and may be flexible speculum 810. Components of the same name or implied functionalities may correspond to those of the respective speculum. All of the dimensions discussed with respect to the speculum are examples, and speculums of different sizes may be implemented.

Optionally, a speculum 100 has a diameter less than or equal to 2 mm and 4.5 mm. Speculum 100 can be configured to have a length of around 20-40 mm.

Speculum 100 can include, as described for example herein, a lens 510 and a protective cover 420 that can act as a Light diffuser. Lens 510 can have a diameter in range of 0.7 mm-1.25 mm.

Speculum 100 can include one or more sensors 730 such as a Complementary metal-oxide-semiconductor (CMOS) or a CCD (charge-coupled device) chip for imaging. Sensor 730 can be located inside an imaging module 740.

LEDs 530 and/or other light sources, for example as describe herein can be located on the LED board 620.

Speculum 100 can include an electrical board processor. Speculum 100 can be configured to have a watertight seal for water and cleaning fluid protection.

Speculum 100 can include one or more controllers 770, processors and/or other devices for controlling LEDs 530 and sensor 730 in unison, separately, in an automatic, preset, and/or other fashion.

Speculum 100 can include one or more connectors 120, for example as described herein for connection to other devices, and/or boards.

Speculum 100 can include a flexible holder 790, and/or other body (e.g. a body that can also be used as holder), protective sheath, cover, and/or component. Flexible holder 790 can be configured to have a watertight seal for water and cleaning fluid protection. Connector 795 is used to attach and hold protective covers or stoppers to the speculum module.

FIG. 14 is a schematic depiction illustrating a set of connectors for a speculum, in accordance with the presently disclosed subject matter. The speculum of FIG. 14 may be speculum 100 and may be flexible speculum 810. Components of the same name or implied functionalities may correspond to those of the respective speculum.

A connection component 910 of a speculum, for example, as described herein can be configurable to provide multiple types of connections to one or more devices, including for example, standard, proprietary and/or other devices.

Connectivity from connection component 910 can be through one or more connectors 910, wherein connectors 910 can be situated in one or more patterns. Connectivity can provide, power, communication, light and/or other connectivity. Power can be provide directly and/or through proximity, wireless, inductive and/or other methodologies of powering.

Optionally, connectors 910 can provide a proprietary connectivity to one or more devices. Connectors 910 can vary in size, number and/or placement and can be configurable to move, be removed, and or otherwise vary for use in one or more connection types. Optionally, connection component 910 can be removable and/or replaceable.

Connectors 910 can be configurable to provide wired and/or wireless communication. Connectors 910 can be configurable to provide additional light sources, for example, infrared, ultraviolet and/or other light sources to an optical unit, for example, optical unit described herein.

FIG. 15 is a flowchart illustrating an example of method 1900 for using a speculum, in accordance with the presently disclosed subject matter. Referring to the examples set forth with respect to the previous drawings, method 1900 may be used for using speculum 100, speculum 800, and may be extended—mutatis mutandis—for using otoscope 800.

It is noted that stages 1050, 1060 and 1090 are mandatory, and that all the rest of the stages of method 1900 (i.e. stages 1010, 1020, 1030, 1040, 1070, 1080 and 1100) are optional. Any combination including stages 1050, 1060 and 1090—and any one or more of stages 1010, 1020, 1030, 1040, 1070, 1080 and 1100 may also be implemented as method 1900.

A user, for example a health professional, parent, sibling, friend, colleague, self, and/or other person begins the process of examining a body part, Optionally an orifice, for example an ear, to assess, medically, recreationally, or otherwise the status of a part of the body, for example the eardrum of a child, sick individual, or animal. The process can include the use of a speculum described herein. The speculum can be used in conjunction with one or more devices. The speculum can be configured for use with a local network, and/or may need to be configured to be used with a network. The speculum can be configured for use, and/or the speculum may need to be calibrated for use. The speculum can be in a powered on state, a standby state, and/or another state related to power. The beginning of the process of examination as depicted, for example, by box 1000.

The size of the speculum and/or other device relative to the body part to be examined or access to said body part, for example the size of an ear canal is assessed, for example as depicted in diamond 1010. Optionally, the speculum and/or other device may need a stopper to provide a necessary width, girth, length and/or other characteristics for a particular individual's ear canal, and/or other body part and/or access thereto. Optionally, when a stopper, for example, protective stoppers described herein, a stopper can be attached, coupled, and/or otherwise associated with the speculum and/or other devices, the attaching of the stopper as depicted in box 1020. Referring to the examples set forth with respect to the previous drawings, the stopper of stage 1020 may be stopper 340 and/or stopper 820.

Optionally, for example a home setting a speculum and/or other device can be sufficiently cleaned and/or otherwise disinfected for use with one or more individuals and/or body parts. Optionally, for example, in a clinical or public setting, a speculum and/or other device cannot be sufficiently cleaned, presented, and/or otherwise disinfected for use with one or more individuals. Determining whether a cover is necessary in lieu of and/or in addition to cleaning and/or disinfecting is depicted in diamond 1030. A cover can be connected to a speculum, as depicted in box 1040, the connection described for example above. Referring to the examples set forth with respect to the previous drawings, the cover of stage 1030 may be cover 420 and/or cover 870.

A speculum, covered or uncovered is inserted into an orifice and/or in close proximity with a body part to be examined, for example the ear canal to examine the eardrum, the insertion as depicted in box 1050.

Optionally, the use of a speculum and/or other device can be done in real-time or near real-time with a health care provider and/or physician. In some examples the speculum is operated independently by a non-medical user. The determination of control as depicted in diamond 1060.

A device, for example, the speculum, operated by a user can be aligned manually to capture images of the body part, the manual usage as depicted by box 1070. Optionally, the user is directed in real time by a physician, and/or medical professional, remotely. The device, for example the speculum can provide feedback, for example haptic and/or audible feedback to help the user align the device, the feedback, for example as controlled remotely by a physician and/or other individual, the remote direction depicted, for example by box 1080.

Optionally the device can be configured to provide automatic, and/or semi-automatic feedback to a user to facilitate the proper, useful, optimal and/or necessary placement of the device. Optionally the device can be configured to capture image or video autonomously and/or semi-autonomously.

Images, including in some examples video are captured, the capturing as depicted in box 1090.

Captured images can be uploaded and/or streamed immediately or after a set time to a medically trained individual, the uploading as depicted in box 1100.

During the ear exam speculum or attached device could produce variety of sounds that could help during examination process. For example, it could be guidance sound that inform the penetration depth or image quality for adult patients or pleasant and child likeable sounds to draw child attention and prevent movements.

FIGS. 16A and 16B are flow charts illustrating examples of method 1500 for intraaural imaging, in accordance with the presently disclosed subject matter. Referring to the examples set forth with respect to the previous drawings, method 1500 may be executed by a user operating otoscope 800. Referring to the examples set forth with respect to the previous drawings, method 1500 may be executed by a user operating speculum 100. The user may be the same person whose eardrum is images in method 1500, but this is not necessarily so. The user may be a medical expert (e.g. a physician, a nurse, a technician) or a layperson (e.g. a family member, an elementary school teacher). The term "intraaural" pertain to things, actions or conditions which take place inside the ear. Within the scope of the present disclosure, the term refers especially to things, actions or condition which take place inside the ear canal.

It is noted that stages 1530 and 1590 are mandatory, and that all the rest of the stages of method 1500 are optional. Any combination including stages 1530, 1590—and any one or more of the other optional stages of method 1500 may also be implemented as method 1500.

Stage 1530 of method 1500 includes inserting a flexible speculum into an ear canal, so that the inserting causes bending of the flexible speculum inside the ear canal, thereby aligning an imaging sensor included in the flexible speculum according to a shape of the ear canal. The direction of inserting is from outside the ear, towards the ear drum. The inserting may be executed when the user holds the flexible speculum itself, or a device connected to the flexible speculum, such as a handle, or a medical monitoring electronic device.

Stage 1590 takes place after the imaging sensor captures an image of an eardrum of the ear canal, stage 1590 includes removing the flexible speculum from the ear canal. The removing may be executed by pulling the flexible speculum itself, and may be executed by pulling a device connected to the flexible speculum.

It is noted that the different aspects discussed with respect to flexible speculum 810 above may also apply to the flexible speculum of method 1500.

The optionally, the inserting of stage 1530 may include inserting the flexible speculum which includes a rigid tip which includes the imaging sensor and a flexible part coupling the rigid tip and a base of the flexible speculum.

The optionally, the inserting of stage 1530 may include inserting the flexible speculum to the ear canal to a depth in which a bending of the flexible speculum blocks any line of sight between a leading plane of the flexible speculum and a base of the flexible speculum.

The optionally, the inserting of stage 1530 may divert an optical axis of the imaging sensor by at least 10 degrees with respect to a longitudinal axis of a back part of the flexible speculum at a time in which the imaging sensor captures the image of the eardrum.

The optionally, the inserting of stage 1530 may include inserting the imaging sensor to the ear canal when an auricle of the ear canal is at its rest position, wherein the rest position of the auricle is such which does not provide a line of sight to the eardrum from outside the ear canal.

Method 1500 may also include stage 1610, of capturing one or more images of the eardrum (and possibly other intraaural images as well) by the imaging sensor. The term image may pertain to standalone images and/or to images which are part of a video. Referring to the examples set forth with respect to the previous drawings, stage 1610 may be executed by imaging sensor 830. Stage 1610 may be triggered by the same user which executes stage 1530 (or another person)—e.g. by operating a user interface connected to a controller of the imaging sensor (e.g. processor 850). Stage 1610 may be triggered by part of an otoscope of which the flexible speculum is a component. Stage 1610 may be triggered by an external system (e.g. operated by a physician located at a remote location).

Method 1500 may also include stage 1690, which includes sending image data based on one or more images captured by the imaging sensor to a remote location. Referring to the examples set forth with respect to the previous drawings, stage 1690 may be executed by communication unit 890. Stage 1690 may be triggered by the same user which executes executing stage 1530 (or another person)—e.g. by operating a user interface connected to a controller of the imaging sensor (e.g. processor 850). Stage 1610 may be triggered by part of an otoscope of which the flexible speculum is a component. Stage 1610 may be triggered by an external system (e.g. operated by a physician located at a remote location). It is noted that the triggering of stage 1690 may be a derivative triggering. For example, the user (or the external system) may trigger stage 1610, and the successful completion of stage 1610 may trigger the execution of stage 1690.

FIG. 17 is a flow chart illustrating an example of method 1500 for intraaural imaging, in accordance with the presently disclosed subject matter. The flexible speculum of method 1500 may have a stopper connected to it. Referring to the examples set forth with respect to the previous drawings, the stopper may be stopper 820. Referring to the examples set forth with respect to the previous drawings, the stopper may be stopper 340. The stopper may be used by the user of method 1500 for stopping the insertion of the flexible speculum into the ear canal.

Method 1500 may include stage 1540 of stopping the insertion of the flexible speculum into the ear canal when the stopper (connected to the flexible speculum) limits further penetration of the flexible speculum into the ear canal. As discussed with respect to otoscope 800, the stopper may be connected directly to flexible speculum, or indirectly. In the latter case, both the flexible speculum and the stopper are connected to a shared support (again, either directly or indirectly). For example, the stopper may be connected to a base of an otoscope, to a handle of an otoscope, to a handheld computer (e.g. a smartphone, a propriety device), and so on.

As discussed with respect to the speculums above, the stopper may stop or limit insertion of the flexible speculum into the ear canal in different ways. For example, the stopper may be wider than the ear canal.

Optionally, the user may determine the allowed penetration depth of the stopper into the ear canal (denoted stage 1510). This may be achieved in different ways, e.g. by executing stage 1512 and/or 1514. Optional stage 1510 takes place prior to the inserting.

Stage 1512 includes mechanically configuring a penetration depth limit allowed by the stopper (which is connected to the flexible speculum and which limits a penetration depth of the flexible speculum into the ear canal). Some of the possible ways for configuring the allowed penetration depth are discussed above with respect to the previous drawings.

Stage 1514 includes selecting a stopper out of a plurality of different stoppers, and connecting the selected stopper to the flexible speculum, for limiting a penetration depth of the flexible speculum into the ear. The connecting may be a direct connection or an indirect connection, as discussed above.

Method 1500 may also include stage 1520, executed prior to the inserting, which includes covering the flexible speculum with a flexible cover which includes an optical tip which allows transmission of light through the optical tip to the imaging sensor.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It will be appreciated that the embodiments described above are cited by way of example, and various features thereof and combinations of these features can be varied and modified.

While various embodiments have been shown and described, it will be understood that there is no intent to limit the invention by such disclosure, but rather, it is intended to cover all modifications and alternate constructions falling within the scope of the invention, as defined in the appended claims.

What is claimed is:
1. An otoscope, the otoscope comprising:
a flexible speculum, operable to be inserted into an ear canal, the flexible speculum comprising:

a rigid tip including a digital imaging sensor operable to capture an image of an eardrum of the ear canal, the rigid tip being at a distal end of the flexible speculum; and a flexible part coupling the rigid tip and a base of the flexible speculum, wherein the flexible part has a first flexibility, enabling the flexible speculum to bend, during an insertion thereof into the ear canal, in a manner that blocks any line of sight between a leading plane of the flexible speculum and the base of the flexible speculum, wherein the rigid tip has a second flexibility that is less than the first flexibility; and wherein the digital imaging sensor is capable of capturing the image of the eardrum when a bending of the flexible speculum blocks any line of sight between the leading plane of the flexible speculum and the base of the flexible speculum.

2. The otoscope according to claim 1, wherein the otoscope further comprises a stopper, coupled to the flexible speculum, operable to limit penetration depth of the flexible speculum into the ear canal, and wherein the stopper is wider than the ear canal.

3. The otoscope according to claim 2, wherein the stopper is mechanically configurable to limit the penetration of the flexible speculum into the ear canal to different depths.

4. The otoscope according to claim 2, wherein the stopper is one of a plurality of different sized stoppers, and wherein each of the different sized stoppers is capable of being detachably coupled to the flexible speculum.

5. The otoscope according to claim 2, wherein a first distance of the digital imaging sensor from the leading plane of the flexible speculum is smaller than a quarter of a second distance between the stopper and the leading plane.

6. The otoscope according to claim 1, wherein the rigid tip further includes at least one light source, operable to light at least part of the ear canal.

7. The otoscope according to claim 1, wherein the digital imaging sensor is operable to capture the image of the eardrum when an optical axis of the digital imaging sensor and a longitudinal axis of a back part of the flexible speculum define an angle of at least 10 degrees.

8. The otoscope according to claim 1, wherein the digital imaging sensor is operable to capture the image of the eardrum when an auricle of the ear canal is at its rest position, wherein the rest position of the auricle is such which does not provide a line of sight to the eardrum from outside the ear canal.

9. The otoscope according to claim 1, further comprising a flexible cover for covering the flexible speculum, the flexible cover comprising an optical tip which is operable to transfer light from the eardrum to the digital imaging sensor.

10. The otoscope according to claim 9, further comprising a coupling for detachably coupling the flexible cover and the flexible speculum.

11. The otoscope according to claim 1, further comprising a physiological sensor positioned inside the flexible speculum, the physiological sensor is operable to measure a nonvisual physiological parameter inside the ear canal.

12. A method for intraaural imaging, the method comprising:

inserting a flexible speculum into an ear canal, the flexible spectrum comprising: (a) a rigid tip including a digital imaging sensor, the rigid tip being at a distal end of the flexible speculum and (b) a flexible part coupling the rigid tip and a base of the flexible speculum, wherein the flexible part has a first flexibility, wherein the rigid tip has a second flexibility that is less than the first flexibility, and wherein the inserting causes bending of the flexible speculum inside the ear canal; and after the digital imaging sensor captures an image of an eardrum of the ear canal, removing the flexible speculum from the ear canal;

wherein the digital imaging sensor is capable of capturing the image of the eardrum when the bending of the flexible speculum blocks any line of sight between a leading plane of the flexible speculum and the base of the flexible speculum; and wherein the first flexibility of the flexible part enables the flexible speculum to bend, during the inserting, to block any line of sight between the leading plane of the flexible speculum and the base of the flexible speculum.

13. The method according to claim 12, further comprising stopping the insertion of the flexible speculum into the ear canal when a stopper coupled to the flexible speculum limits further penetration of the flexible speculum into the ear canal.

14. The method according to claim 13, wherein the stopper is wider than the ear canal.

15. The method according to claim 13, wherein the inserting is preceded by mechanically configuring a penetration depth limit allowed by the stopper.

16. The method according to claim 13, wherein the inserting is preceded by selecting the stopper out of a plurality of different stoppers, and coupling the stopper to the flexible speculum, for limiting a penetration depth of the flexible speculum into the ear.

17. The method according to claim 12, wherein the inserting comprises inserting the flexible speculum to the ear canal to a depth in which the bending of the flexible speculum blocks the any line of sight between the leading plane of the flexible speculum and the base of the flexible speculum.

18. The method according to claim 12, wherein the inserting diverts an optical axis of the digital imaging sensor by at least 10 degrees with respect to a longitudinal axis of a back part of the flexible speculum at a time in which the digital imaging sensor captures the image of the eardrum.

19. The method according to claim 12, wherein the inserting comprises inserting the digital imaging sensor to the ear canal when an auricle of the ear canal is at its rest position, wherein the rest position of the auricle is such which does not provide a line of sight to the eardrum from outside the ear canal.

20. The method according to claim 12, wherein the inserting is preceded by covering the flexible speculum with a flexible cover which comprises an optical tip which allows transmission of light through the optical tip to the digital imaging sensor.

* * * * *